United States Patent
Jaquish et al.

(10) Patent No.: US 11,792,611 B2
(45) Date of Patent: *Oct. 17, 2023

(54) SECURE MESSAGING SYSTEM WITH CONSTRAINED USER ACTIONS, INCLUDING OVERRIDE, FOR ENSURED COMPLIANT TRANSMISSION OF SENSITIVE INFORMATION

(71) Applicant: TEXTLINE, INC., San Francisco, CA (US)

(72) Inventors: Marshall Jaquish, Rocklin, CA (US); Jordan Gadapee, Round Rock, TX (US); Randall Berg, Coral Gables, FL (US); Mark Lilien, Costa Mesa, CA (US)

(73) Assignee: Textline, Inc., San Francisco, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 17/305,629

(22) Filed: Jul. 12, 2021

(65) Prior Publication Data

US 2022/0103980 A1     Mar. 31, 2022

Related U.S. Application Data

(63) Continuation-in-part of application No. 17/037,155, filed on Sep. 29, 2020, now Pat. No. 11,062,809.

(51) Int. Cl.
*G06F 9/451* (2018.01)
*H04W 4/14* (2009.01)
(Continued)

(52) U.S. Cl.
CPC ............ *H04W 4/14* (2013.01); *G06F 3/0485* (2013.01); *G06F 3/04842* (2013.01); *H04L 51/212* (2022.05); *H04L 51/58* (2022.05)

(58) Field of Classification Search
CPC ......... H04W 4/14; H04W 4/12; H04W 12/08; G06F 3/04842; G06F 3/0485;
(Continued)

(56) References Cited

U.S. PATENT DOCUMENTS

| 7,363,489 B2 * | 4/2008 | Burakoff ............... G06F 40/134 |
| | | 713/153 |
| 7,647,320 B2 | 1/2010 | Mok et al. |

(Continued)

FOREIGN PATENT DOCUMENTS

WO     WO 2001/006433 A1     1/2001

OTHER PUBLICATIONS

Hanauer, David A., et al., "Computerized Automated Reminder Diabetes System (CARDS): E-Mail and SMS Cell Phone Text Messaging Reminders to Support Diabetes Management," Diabetes Technol Ther, Feb. 1, 2009; 11(2): 99-106.

(Continued)

*Primary Examiner* — Hien L Duong
(74) *Attorney, Agent, or Firm* — Knobbe, Martens, Olson & Bear, LLP

(57) ABSTRACT

Systems and methods are provided for secure messaging with constrained user actions. An example method includes causing presentation of an interactive user interface, the interactive user interface enabling messaging with end users, each end user being associated with a respective phone number. Selection of a particular end user is received via the interaction user interface and the interactive user interface is updated to include a selectable option which triggers transmission of a standardized consent message to a particular phone number associated with the particular end user. User input is received which indicates receipt of externally provided affirmative consent. The interactive user interface is updated, with the updated interactive user interface includ- (Continued)

ing an input portion configured to receive arbitrary information for transmission to the particular phone number.

20 Claims, 27 Drawing Sheets

(51) Int. Cl.
  *G06F 3/0485* (2022.01)
  *G06F 3/04842* (2022.01)
  *H04L 51/58* (2022.01)
  *H04L 51/212* (2022.01)
(58) Field of Classification Search
  CPC .... G06F 3/0482; G06F 21/606; G06F 16/953; G06F 9/451; H04L 51/212; H04L 51/58; H04L 51/214; H04L 51/56; H04L 51/18; G16H 40/67; G16H 80/00; G16H 10/60; G06Q 30/016
  See application file for complete search history.

(56) References Cited

U.S. PATENT DOCUMENTS

| | | | |
|---|---|---|---|
| 7,729,929 B2 | 6/2010 | Heidenreich et al. | |
| 8,132,110 B1 | 3/2012 | Appelman et al. | |
| 8,358,771 B1 | 1/2013 | Moore et al. | |
| 8,620,683 B2 | 12/2013 | Findlay et al. | |
| 9,934,544 B1 | 4/2018 | Whitfield et al. | |
| 10,572,107 B1 | 2/2020 | Beebe et al. | |
| 10,623,567 B1 | 4/2020 | Perdue et al. | |
| 10,630,673 B1 | 4/2020 | Lingampally et al. | |
| 10,750,021 B1 | 8/2020 | Koster et al. | |
| 11,062,809 B1 | 7/2021 | Jaquish et al. | |
| 2002/0062228 A1 | 5/2002 | Portnoy et al. | |
| 2002/0065682 A1 | 5/2002 | Goldenberg | |
| 2002/0065896 A1 | 5/2002 | Burakoff et al. | |
| 2005/0027568 A1 | 2/2005 | Dorris | |
| 2006/0047748 A1 | 3/2006 | Kelso et al. | |
| 2008/0077431 A1 | 3/2008 | Calder et al. | |
| 2008/0133273 A1 | 6/2008 | Marshall | |
| 2010/0094650 A1 | 4/2010 | Tran et al. | |
| 2011/0074909 A1* | 3/2011 | Sadafule | H04N 7/147 348/14.1 |
| 2011/0113101 A1 | 5/2011 | Ye et al. | |
| 2011/0218410 A1 | 9/2011 | Buisman et al. | |
| 2011/0252153 A1 | 10/2011 | Vlodavsky | |
| 2012/0030588 A1 | 2/2012 | Sinha | |
| 2012/0116815 A1 | 5/2012 | Lorsch | |
| 2012/0265681 A1 | 10/2012 | Ross | |
| 2013/0067340 A1 | 3/2013 | Appelman et al. | |
| 2013/0162750 A1 | 6/2013 | Nerst et al. | |
| 2013/0254288 A1 | 9/2013 | Harrison | |
| 2013/0332193 A1 | 12/2013 | Kiselev et al. | |
| 2014/0351368 A1 | 11/2014 | Dudziak et al. | |
| 2015/0025911 A1 | 1/2015 | Altebrando et al. | |
| 2015/0127561 A1* | 5/2015 | Heller | G06Q 30/018 705/317 |
| 2015/0154357 A1 | 6/2015 | Biswas et al. | |
| 2015/0213195 A1 | 7/2015 | Blechman | |
| 2016/0132696 A1 | 5/2016 | Vidhani et al. | |
| 2016/0357916 A1 | 12/2016 | Willard et al. | |
| 2017/0111300 A1 | 4/2017 | Devasthali et al. | |
| 2017/0214645 A1 | 7/2017 | Berkow et al. | |
| 2017/0214663 A1 | 7/2017 | Berkow et al. | |
| 2018/0039737 A1 | 2/2018 | Dempers et al. | |
| 2018/0082024 A1 | 3/2018 | Curbera et al. | |
| 2018/0213020 A1 | 7/2018 | Kakutani et al. | |
| 2019/0036856 A1 | 1/2019 | Bergenlid et al. | |
| 2019/0348158 A1 | 11/2019 | Livesay et al. | |
| 2019/0354721 A1 | 11/2019 | Livesay et al. | |
| 2019/0379615 A1 | 12/2019 | Karp et al. | |
| 2020/0004987 A1* | 1/2020 | Brannon | G06F 16/958 |
| 2020/0135005 A1 | 4/2020 | Katz et al. | |
| 2020/0167501 A1* | 5/2020 | Brannon | G06F 21/6245 |
| 2020/0186518 A1 | 6/2020 | Shah | |
| 2020/0356695 A1* | 11/2020 | Brannon | G06F 16/2379 |
| 2020/0364224 A1 | 11/2020 | Hay et al. | |
| 2020/0364669 A1 | 11/2020 | Hay et al. | |
| 2020/0374129 A1 | 11/2020 | Dilles et al. | |
| 2021/0019763 A1 | 1/2021 | Helles et al. | |
| 2022/0102014 A1 | 3/2022 | Jaquish et al. | |

OTHER PUBLICATIONS

OhMD—HIPAA Compliant Texting for Doctors, "OhMD Two-Way Texting for Patient Communication," published May 1, 2019 available at https://www.youtube.com/watch?app=desktop&v=UMHEJIUITfc.
Simple Texting, "Text Message Appointment Reminders for Doctors, Medical Offices and Dental Practices," available at https://web.archive.org/web/20200602073521/https://simpletexting.com/quide/text-appointment-reminders-for-doctors-and-dental-offices/ dated Jun. 2, 2020, Printed Apr. 28, 2021.
Solution Reach Platform, "How Solution Reach Works," available at https://web.archive.org/web/20200602221500/https://www.solutionreach.com/solutions/how-solutionreach-works dated Jun. 2, 2020, Printed Apr. 28, 2021.
Ventola, C., "Mobile Devices and Apps for Health Care Professionals: Uses and Benefits," May 2014, P&T 39(5): 356-364.

* cited by examiner

FIG. 11A

FIG. 11B

SECURE MESSAGING SYSTEM WITH CONSTRAINED USER ACTIONS, INCLUDING OVERRIDE, FOR ENSURED COMPLIANT TRANSMISSION OF SENSITIVE INFORMATION

CROSS-REFERENCE TO RELATED APPLICATIONS

This application claims priority to U.S. patent application Ser. No. 17/037,155 titled "SECURE MESSAGING SYSTEM WITH CONSTRAINED USER ACTIONS FOR ENSURED COMPLIANT TRANSMISSION OF SENSITIVE INFORMATION" and filed on Sep. 29, 2020, the disclosure of which is hereby incorporated herein by reference in its entirety.

TECHNICAL FIELD

The present disclosure relates to systems and techniques for messaging, such as web applications for messaging. More specifically, this disclosure relates to applications, such as web applications, to enable messaging of medical information with strict compliance controls.

BACKGROUND

Modern digital messaging tools are increasingly being employed to interact with end users. For example, in lieu of lengthy phone calls, a business may prefer to allow end users, such as patrons, to directly contact the business via a digital messaging tool. In this example, the digital messaging tool may represent an application executing on an end user's mobile device. As another example, the business's website may include functionality to enable input of messages by end users of the website. In this example, the messages may be routed to an application, such as a mobile application or web application, which is accessible to employees of the business. The employees may then quickly respond to any received questions, thus rapidly servicing a number of end users.

While such digital messaging tools are advantageous in certain instances, in other instances they may be disfavored or disallowed. For example, certain types of information, such as private information, may require added technical complexities which reduce usefulness of these digital messaging tools. These added technical complexities may cause businesses, or other entities, to avoid such digital messaging tools. As an example with respect to medical information, ensuring compliance with different regulations may be impractical for the businesses or other entities via these digital messaging tools.

SUMMARY OF CERTAIN EMBODIMENTS

The systems, methods, and devices of this disclosure each have several innovative aspects, no single one of which is solely responsible for the all of the desirable attributes disclosed herein.

Although certain embodiments and examples are disclosed herein, inventive subject matter extends beyond the examples in the specifically disclosed embodiments to other alternative embodiments and/or uses, and to modifications and equivalents thereof.

The details, including optional details, of one or more embodiments of the subject matter of this specification are set forth in the accompanying drawings and the description below. Other optional features, aspects, and advantages of the subject matter will become apparent from the description, the drawings, and the claims.

BRIEF DESCRIPTION OF THE DRAWINGS

Throughout the drawings, reference numbers are re-used to indicate correspondence between referenced elements. The drawings are provided to illustrate embodiments of the subject matter described herein and not to limit the scope thereof.

FIG. 11A is an example user interface illustrating identification of an end user who is to be messaged.

FIGS. 11B-C are example user interfaces illustrating interaction with a manual override option.

Like reference numbers and designations in the various drawings indicate like elements.

DETAILED DESCRIPTION

Introduction

Figure 1A:
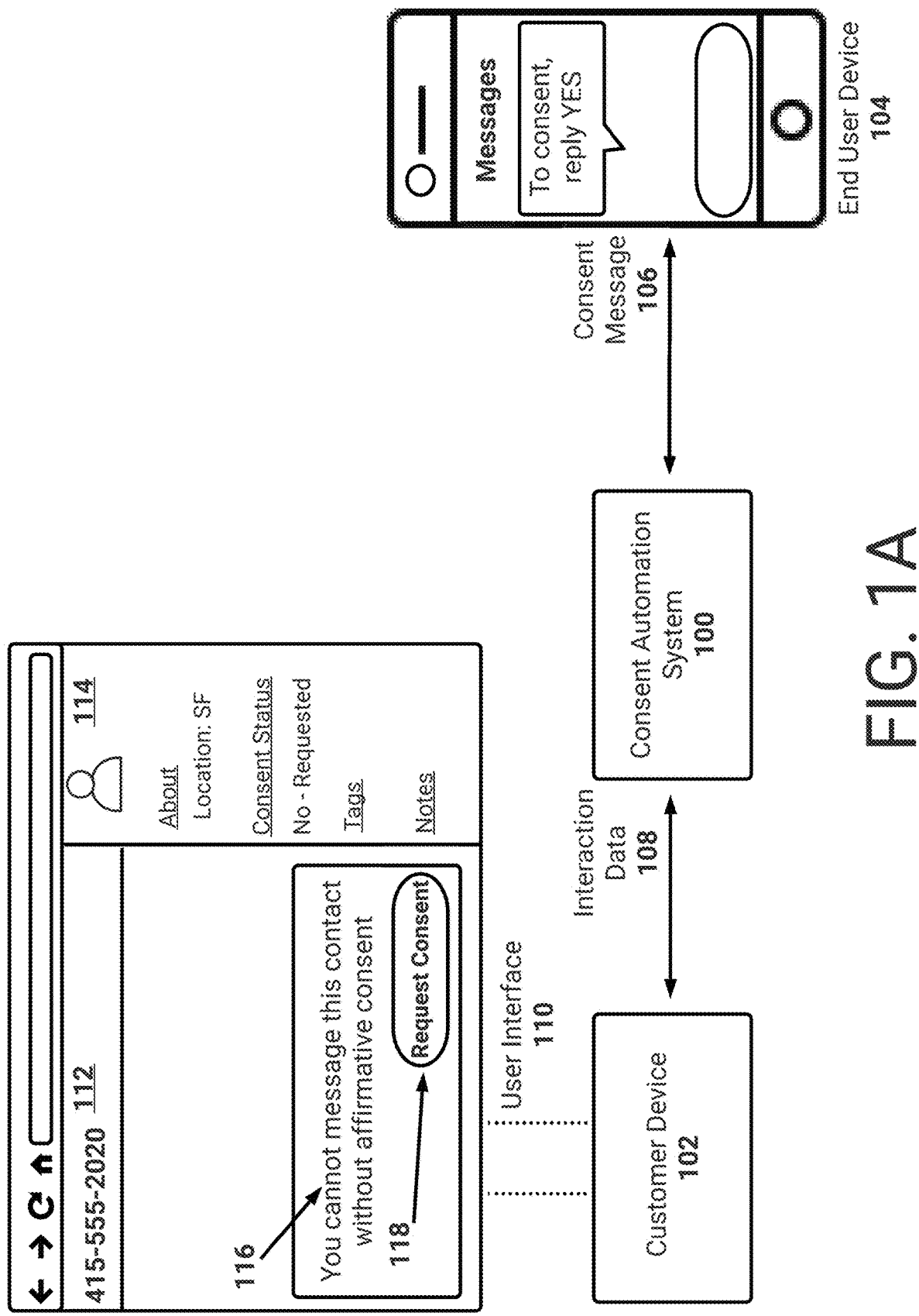
FIG. 1A illustrates a block diagram of an example consent automation system providing a consent message to an end user device.

This specification describes, among other things, an improved digital messaging tool which ensures strict compliance with regulations associated with use of sensitive information. As will be described, the digital messaging tool may be implemented by a system described herein (e.g., the consent automation system 100). The digital messaging tool may represent an application, such as a web application, which is accessible via an interactive user interface. Employees of an entity, such as employees of a business or hospital, (herein referred to as 'customer users') may use the digital messaging tool to directly provide sensitive information to persons who patronize the entity (herein referred to as 'end users'). As an example, the digital messaging tool may directly message sensitive information to end users via insecure messaging techniques. Example insecure messaging techniques may include short messaging service (SMS) or multimedia messaging service (MMS) text messages.

Advantageously, the digital messaging tool ensures that end users have consented to receiving such direct messages by constraining actions the customer users can perform via the tool. For example, the customer users may be unable to send arbitrary messages to end users absent confirmed consent. In this way, the digital messaging tool creates inescapable compliance supporting boundaries and improves upon prior digital messaging tools and platforms.

As an example described herein, the digital messaging tool may allow for customer users to provide medical information to end users. Example customer users may include persons who are associated with the use of, or storing of, medical information, such as medical professionals, doctors, nurses, pharmacists, insurance employees, and so on. Example customer users may further include persons who are associated with other sensitive information, such as financial information. Example end users may include patients, persons who use a pharmacy, persons who are customers of a health insurance company, persons who are involved in clinical trials, and so on. Example end users may further include persons who use a financial planner. With respect to medical information, medical professional users may represent customer users and patients may represent end users.

It may be appreciated that texting, such as SMS or MMS texting, is a universal feature of mobile devices carried by end users. End users may therefore appreciate the ease of receiving information via this known technology. For example, an end user may appreciate being alerted by a pharmacy that his/her pharmaceutical is ready for pick up. Similarly, a customer user with the pharmacy may prefer the ease associated with merely messaging an end user. In contrast, other tools to provide information to end users may rely upon bespoke applications which need to be obtained from online application stores (e.g., 'apps'). End users may be required to create user accounts specifically for use with these applications. This may reduce a likelihood that end users will leverage such messaging applications.

Thus, providing direct text messages to end users may improve a user experience associated with receiving sensitive information. However, and as described below, certain types of sensitive information may require technical complexities surrounding the providing of the sensitive information. For example, medical information may require affirmative consent by an end user before a customer user is allowed to directly message the end user via insecure techniques (e.g., texting). As described below, with respect to a first example digital messaging tool, current techniques to handle such consent are lacking. Thus, a second example digital messaging tool is described herein which improves upon these prior digital messaging tools.

While the description herein focuses on medical information, the digital messaging tool described herein may allow for sending of arbitrary sensitive information. By the automated consent technique described herein, which ensures strict compliance with end user consent, the arbitrary sensitive information may be safely provided to end users.

Introduction—Medical Information

As may be appreciated, medical information is typically considered among the most sensitive forms of personal information. Indeed, there are a plethora of rules, regulations, and constraints, associated with the use of such medical information. An example regulation in the United States includes the Health Insurance Portability and Accountability Act (HIPAA) which places strict limitations regarding the dissemination and flow of medical information. For example, covered entities are required to follow complex regulations regarding the maintaining, and providing, of protected health information of persons. Other countries have similar restrictions.

These complex regulations require, among other things, complexities surrounding the provision of medical information to end users. For example, hospitals may typically use secure email platforms to provide medical information to patients. These secure email platforms may require a multi-step process for a patient to access the provided medical information. As an example, the patient may be required to download a specific application including the secure email platform and set up and maintain a separate user account with the secure email platform. The patient may be required to navigate to a specific website and access his/her separate user account associated with the secure email platform before accessing the provided medical information.

Other messaging techniques may be allowed, such as insecure direct messaging to patients' email address, but the patients may be required to affirmatively consent to such messaging techniques. This affirmative consent may introduce technical complexities which cause entities to avoid such direct messaging techniques. In this way, end users may not obtain the benefits which are afforded by such direct messaging. For example, and as described above, a pharmacy may prefer to simply provide a direct text message to an end user when his/her prescription is ready. In this example, the pharmacy may be unable to ensure strict compliance with all of their end users having provided consent.

The above-described pharmacy may represent a chain with thousands of stores and millions of end users who purchase pharmaceuticals. Ensuring that each end user has authorized direct messaging may be fraught with technical errors and technical complexities which may result in a failure to comply with HIPAA or other privacy laws and regulations. Additionally, even with a technique to identify whether authorization has been received, it may be impractical to ensure that employees of the pharmacy chain are complying with such authorizations. This may lead to an employee text messaging an end user who has not yet provided authorization. The end user may have also provided authorization and then revoked it, and the pharmacy's records may not have been updated to reflect this revocation. In this way, the pharmacy may revert to other messaging techniques (e.g., phone calls).

First Example Digital Messaging Tool

To provide an easy to utilize messaging platform, an entity may use a digital messaging tool which is accessible to employees of the entity. The digital messaging tool may be accessible as a mobile application or software which is available on user devices of the employees. The digital messaging tool may also be associated with a web application that is accessible via a browser on user devices of the employees. An employee may interact with the digital messaging tool to select an end user, such as a patient, to receive a direct message. The employee may then provide information to the end user via a direct message. The digital messaging tool may then transmit the information as a short messaging service (SMS) or multimedia messaging service (MMS) text message. With respect to the example of a pharmacy, the employee may provide information indicating that a particular pharmaceutical is ready for pickup by the end user. In this way, the digital messaging tool may provide an easy front-end user interface for all customer users to utilize when messaging end users.

As may be appreciated, there may be errors associated with use of this digital messaging tool. For example, an employee may directly message an end user with medical information. The employee may subsequently request that the end user consent to receiving digital messages. For example, the employee may provide a message saying, 'your test results are positive, can you please authorize us to provide the results to you?' Since protected health information may have been provided by this message without receipt of consent, a HIPAA violation may occur Lacking a mechanism by which consent may be assured prior to transmitting medical information, an entity who uses the first example digital messaging tool may thus be unable to ensure compliance with HIPAA.

Second Example Digital Messaging Tool

In contrast to the first example digital messaging tool, a second example digital messaging tool described herein may ensure compliance with HIPAA or other privacy laws and regulations. The second digital messaging tool may disallow customer users from creating arbitrary messages to an end user without first receiving affirmative consent from the end user, regardless of whether the interaction is initiated by the customer user or the end user. As will be described, an interactive user interface of the second digital messaging tool may only allow a customer user to provide a standardized consent message to an end user. This standardized consent message may be provided as an SMS or MMS text message and may request that the end user respond to indicate affirmative consent. The standardized consent message may be automatically generated upon the system determination that consent is not yet recorded for the particular end user. Upon receipt of such affirmative consent, the interactive user interface may automatically update to allow for arbitrary direct messaging with the end user.

Advantageously, prior to receipt of affirmative consent by an end user, the interactive user interface may only present a selectable option (e.g., a button) which triggers providing the standardized consent message to the end user. This selectable option may represent, in some embodiments, the sole action the customer user can take with respect to messaging the end user. Thus, a customer user may be unable to provide any other information to the end user. For example, the interactive user interface may not include any functionality which enables information to be provided. In this way, actions which the customer user may perform via the interactive user interface are constrained. While a standardized consent message is described above, in some embodiments an entity may allow for customer users to send multiple types or options of consent messages. For example, the different types or options may depend on a type of information at issue or a priority level associated with the information. As another example, the different types or options may be selected according to preference of a customer user.

The above-described end user may thus respond to a received standardized consent message at his/her leisure. Only upon responding with affirmative consent (e.g., "YES") may the interactive user interface of the tool update to allow arbitrary messages to be provided. For example, the customer user may provide information indicating that a particular pharmaceutical is ready for pick-up. As another example, the customer user may provide information indicating a result of certain tests.

Since the second digital messaging tool uses automated techniques to ensure consent, it improves upon the deficiencies of the above-described first digital messaging tool. For example, customer users of the tool may be limited to solely providing standardized consent messages to end users. In this example, an end user may respond indicating that he/she does not consent to such direct messages. As will be described, the interactive user interface of the tool may update to disallow any messages—including the standardized consent messages—from being provided to the end user.

Additionally, end users may automatically receive consent messages from the second digital messaging tool. For example, an end user may provide a direct text message to a phone number at which the second digital messaging tool is responsive. In this example, the end user may initiate contact with an entity via the phone number which may have been provided to the end user by the entity. The second digital messaging tool may automatically respond to the text message with a consent message. The second digital messaging tool may also disallow arbitrary communications with the end user until receipt of affirmative consent from the end user.

As another example, the second digital messaging tool may monitor for receipt of affirmative consent from end users. In this example, the second digital messaging tool may analyze a response received from an end user. For example, the tool may identify whether the end user has provided an exact character string, or a limited number of string choices, identified by the consent message. In this example, the end user may be required to type, "YES" or "I Consent," in a response to the consent message. The tool may store information identifying receipt of this consent. Additionally, the tool may update a consent state associated with the end user. This documented consent state change may be relied upon to ensure compliance with affirmative consent.

The techniques described herein therefore address technical problems and improve upon prior digital techniques for messaging end users. Additionally, the techniques described herein provide for a practical application via use of the enhanced digital messaging tool. For example, an entity may be unable to ensure compliance with required affirmative consent absent the techniques described herein.

Via the succinct, and easy to utilize, user interfaces described herein, the entity may ensure that customer users are properly following HIPAA regulations with respect to affirmative consent. These user interfaces may mask the complexities from customer users associated with ensuring affirmative consent. As an example, and as will be described, an end user not have yet affirmatively consented or indicated negative consent. For this example, the user interface may only allow an action to transmit a consent message to the end user. The user interface may therefore disallow any other messaging actions to the end user. Thus, any customer users are constrained in their ability to violate compliance with HIPAA. This reduces a burden on an entity to train customer users and improves a user experience associated with customer users utilizing digital messaging tools. In this way, the user interfaces improve upon prior user interfaces utilized by digital messaging tools.

The description above focused on an enhanced digital messaging tool which constrains actions via a user interface. As will be described, in some embodiments the techniques described herein may be effectuated by a back-end system. For example, customer users may leverage their preferred messaging application. In this example, SLACK™, ZOOM™, and so on, may be used. A customer user may provide a message to an intended end user which may be routed through the system described herein (e.g., the consent automation system 100). The system may identify whether the end user has provided affirmative consent that he/she prefers to receive sensitive information via insecure direct messaging. If the end user has provided affirmative consent, the system may route the message to the end user as a text message. If the end user has not provided affirmative confirmation, however, the system may block the message from being sent. In some embodiments, the system may instead provide a consent message to the end user (e.g., automatically provide the consent message).

Example Block Diagram

FIG. 1A illustrates a block diagram of an example consent automation system 100 providing a consent message 106 to an end user device 104. The consent automation system 100 is additionally in communication with a customer device 102. The end user device 104 and customer user device 102 may represent mobile devices, tablets, laptops, wearable devices, and so on. As illustrated, the customer device 102 is presenting a user interface 110 associated with a digital messaging tool. As will be described, a customer user utilizing the user interface 110 may cause direct messages to be transmitted to end users. For example, a direct message may represent a text message provided as an SMS or MMS text message to a phone number of an end user. As another example, a message may be provided over an example protocol such as the Rich Communication Services (RCS) protocol, APPLE Push Notification (APN) protocol, and so on.

Direct messages may also represent messages provided via one or more messaging applications. For example, a web application or mobile application may be used to provide messages. In this example, users of the web application or mobile application may be associated with identifying information which may be different from, or in addition to, phone numbers. Example identifying information of a user may include an email address, or a user name, and so on. In some embodiments, the consent automation system 100 may cause messages to be transmitted, or received, via a web application or mobile application. As an example, a customer user may provide a message to a username or email address associated with an end user. In this example, the message may be provided such that it is presented via the web application or mobile application. Similarly, the end user may provide a message to a username or email address associated with the system. Thus, a customer user may view the message received from the end user. With respect to an end user, the consent automation system 100 may determine whether affirmative consent has been received, and if not, may trigger a consent message to the username or email address. In this way, the end user may receive the consent message via the web application or mobile application. Thus, in some embodiments the description herein which focuses on text messages may be applied to messages associated with a web application or mobile application.

The consent automation system 100 may represent a system of one or more computers, one or more virtual machines executing on a system of one or more computers, and so on. As will be described, the consent automation system 100 may implement a web application which is accessible by user devices over a network. In some embodiments, the consent automation system 100 may represent software executing on a cloud platform which is accessible via network connections (e.g., HTTPS connections) to user devices. For example, the system 100 may represent a containerized application associated with a cloud computing network or platform.

The customer device 102 may thus obtain information associated with the user interface 110 from the consent automation system 100. With respect to a web application, the customer device 102 may render the obtained information to present the front-end user interface associated with the web application. Interactions with the user interface 110 may be routed by the customer device 102 for processing by the consent automation system 100. For example, interaction data 108 is illustrated as being provided to the consent automation system 100. Updates to the user interface 110 may thus be effectuated by the consent automation system 100 based on the user input.

In some embodiments, the customer device 102 may execute an application obtained from an application store (e.g., an 'app') which causes presentation of the user interface 110. In these embodiments, the user interface 110 may present information which is obtained from the consent automation system 100. For example, previously sent messages may be included in the user interface 110 based on information obtained from the consent automation system 100.

The user interface 110 includes functionality to provide a message to a particular end user. As will be described, the message may represent a consent message 106 which requests that the end user affirmatively consent to receiving sensitive information, such as medical information, via direct messaging (e.g., texts) as described above. Additionally, and as will be described at least with respect to FIG. 3C, the consent message may automatically be provided to the particular end user. For example, the particular end user may initially provide a message to the system 100 or may initiate contact with the system 100 after a threshold period of time. In response to the message, the system 100 may provide the consent message 106 without interaction with the user interface 110.

In the illustrated embodiment, the customer user has selected a phone number 112 corresponding to end user device 104. The customer user may search for specific end users via search functionality enabled by the user interface 110. As an example, the customer user may type a portion of an end user's name into the user interface 110. The consent automation system 100 may access one or more databases and identify names that are responsive to the portion. As another example, the customer user may type a phone number, email address, or other identifying information into the user interface 110.

Upon selection of an end user to be messaged, the user interface 110 may update to present detailed information 114 associated with the end user. For example, a picture may be presented in the user interface 110. As another example, a location of the end user may be included. Example location information may include a city of residence of the end user, an address of the end user, and so on. As another example, a consent status of the end user may be included in the user interface 110. As will be described, the consent automation system 100 may maintain information for each end user indicating if the end user has provided affirmative consent. In the illustrated example, the end user of the end user device 104 is identified as not having provided affirmative consent. The consent status further indicates that such consent was requested for the end user. As another example, the end user may be associated with tags or notes. Example tags may relate to features or categories associated with the end user.

Since the end user has not yet provided affirmative consent, the user interface 110 constrains the actions which can be performed via the user interface 110. For example, the user interface 110 disallows providing arbitrary messages to the end user. Advantageously, the user interface 110 provides information 116 identifying that consent is required prior to providing messages to the end user.

The user interface 110 includes a selectable option 118 to cause a consent message 106 to be provided to the end user device 104. As illustrated, the user interface limits the actions which may be performed to interaction with this selectable option 118. In this way, the customer user may have no ability to provide any other information to the end user due to the actions performable via the user interface 110. The selectable option 118 may represent a user interface object, such as a button or other element. In some embodiments, the selectable option may be triggered based on user input, such as a mouse click, a touchscreen press, a voice command, and so on.

Figure 3A:
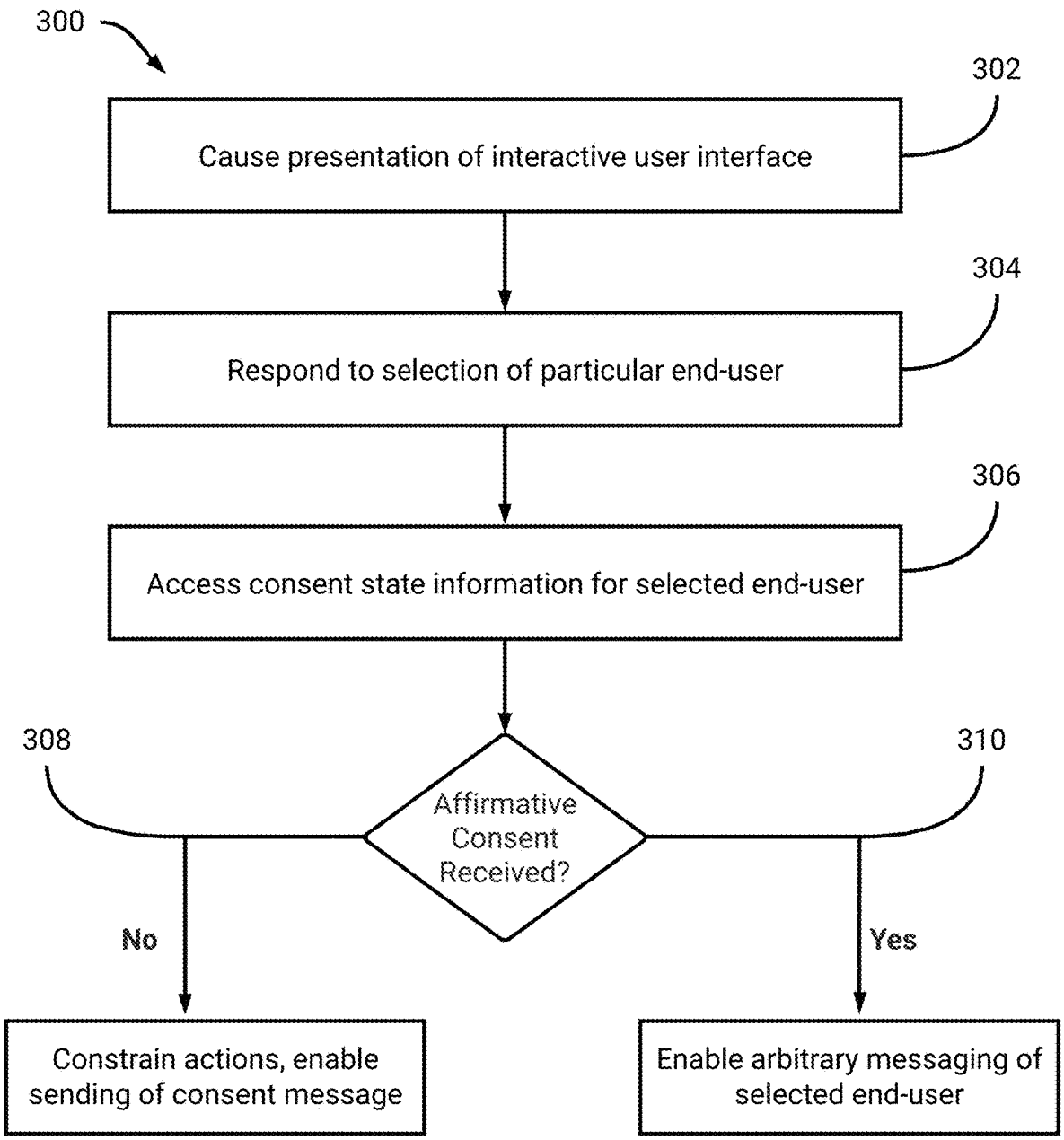
FIG. 3A is a flowchart of an example process for enforcing compliance based on consent messages as described herein.
Figure 3B:
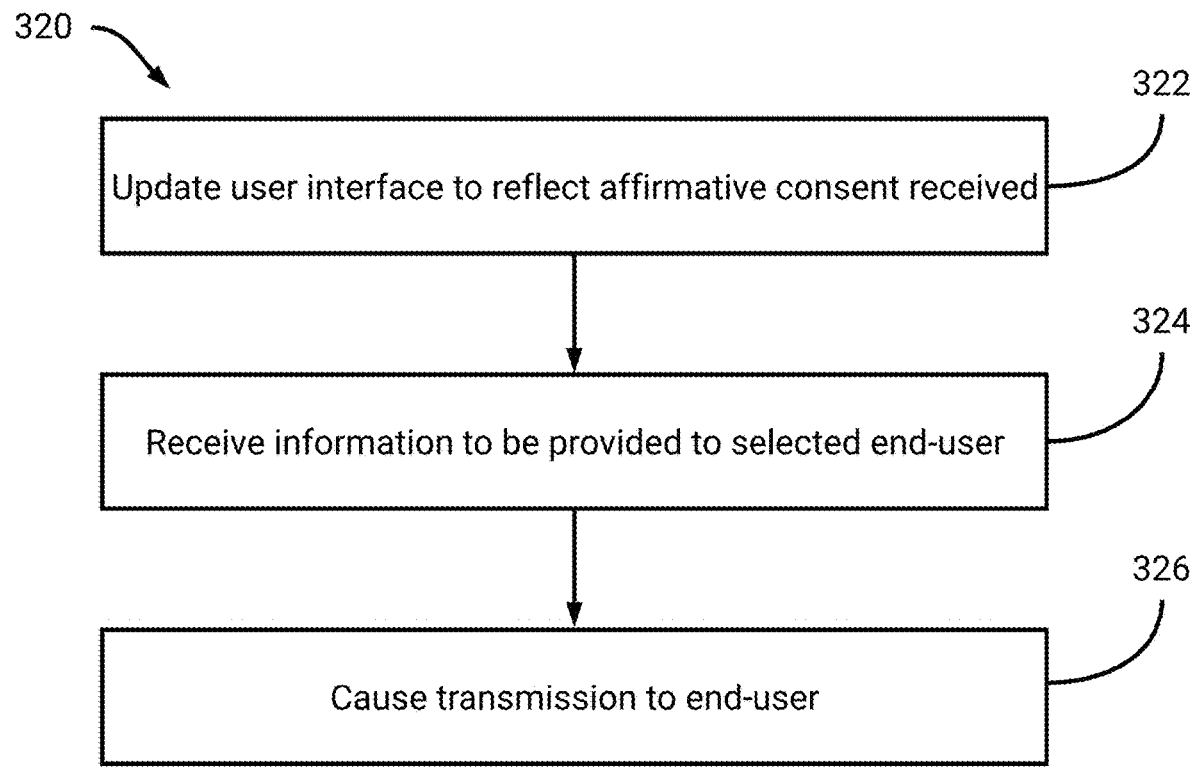
FIG. 3B is a flowchart of a process further describing transmitting arbitrary messages to an end user.
Figure 3C:
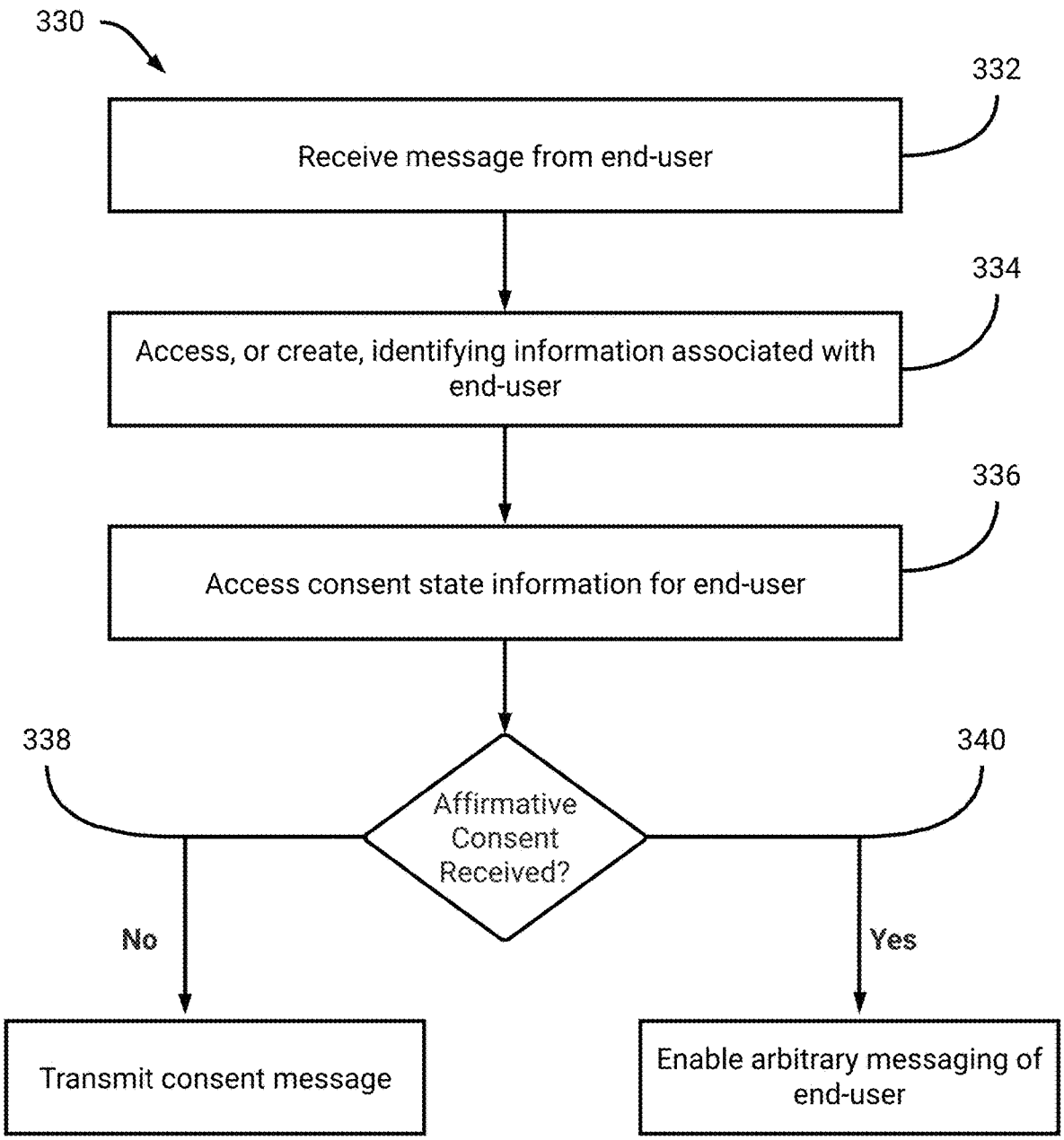
FIG. 3C is a flowchart of an example process for automatically transmitting consent messages to enforce compliance.

In some embodiments, and as described with respect to FIG. 3C, the consent message 106 may be provided to the end user device 104 without interaction with the selectable option 118. For example, the consent message 106 may be provided upon receipt of a text message from the end user device 104. In this example, the system 100 may identify that the consent state associated with the phone number 114 reflects affirmative consent having not been received. As an example, the end user of the end user device 104 may have initiated contact by texting a phone number at which the system 100 receives messages. In response, the system 100 may therefore provide the consent message 106 automatically to the end user device 104 in response. The user interface 110 may present the consent message 106 having been provided (e.g., in chat window 124 illustrated in FIG. 1B).

In some embodiments, the techniques described herein may be implemented at least in part by an intelligent personal assistant (IPA). For example, a customer user may provide voice commands to select an end user. If no affirmative consent has been received, the IPA may identify the lack of consent. The customer user may then request that a consent message is sent to the end user. Once affirmative consent is received, the customer user may verbally speak information to be included in arbitrary text messages to the end user.

Upon interaction with the selectable option 118, interaction data 108 may be provided via the customer device 102 to the consent automation system 100. The consent automation system 100 may then cause the consent message 106 to be directly provided to the end user device 104. For example, the consent automation system 100 may transmit a text message to the phone number 112 associated with the end user device 104. In this example, the consent automation system 100 may execute software associated with transmitting text messages to mobile devices. The consent automation system 100 may also provide information to an outside system, for example via an application programming interface (API), which causes transmission of arbitrary text messages.

The end user device 104 is illustrated presenting the consent message 106 (e.g., via a messaging application, such as a text messaging application). In the illustrated example, the consent message 106 is, "To consent, reply YES." In some embodiments, the consent message 106 may be customized. For example, an entity may specify particular text, images, and so on, to be included in consent messages. An example entity may include a medical professional's office, and the office may specify a unique consent message for use by customer user of the office. As an example, the custom message may include, "This is Doctor Jane's office, to receive medical information from us please respond YES." Customer users associated with the entity may then cause this unique consent message to be transmitted to end users via interaction with the selectable option 118.

The user interface 110 may include functionality to enable the above-described custom messages. For example, the user interface 110 may enable specification of consent messages for all customer users associated with an entity. As another example, the user interface 110 may enable different consent messages for different groups of customer users. In this example, example groups may relate to departments in which customer users work. As another example, the user interface 110 may enable different consent messages according to a type of sensitive information being provided. In this example, an entity may provide different custom consent messages depending on whether an end user is receiving financial information, medical information, and so on. A custom consent message may thus be stored by the consent automation system 100 as being associated with a particular entity. For example, a particular customer user associated with the entity, such as an IT employee, may use a user account which provides authorization to specify custom messages.

The end user of the end user device 104 may therefore determine whether he/she prefers to receive sensitive information over direct message which, in some embodiments, may be insecure. The end user may reply in the negative, such as by providing a message specifying "NO." In response, the consent automation system 100 may update a consent state associated with the end user to indicate that negative consent response has been provided. In some embodiments, and as will be described at least with respect to FIG. 4, the user interface 110 may disallow further communications with the end user by customer users. In some embodiments, the system 100 may assign the negative consent state based on a likelihood that the received text is negative. For example, a deep learning model may be used to assign the likelihood. If the received text is not indicated as negative, the system 100 may maintain the consent state as not having received affirmative consent.

Figure 1B:
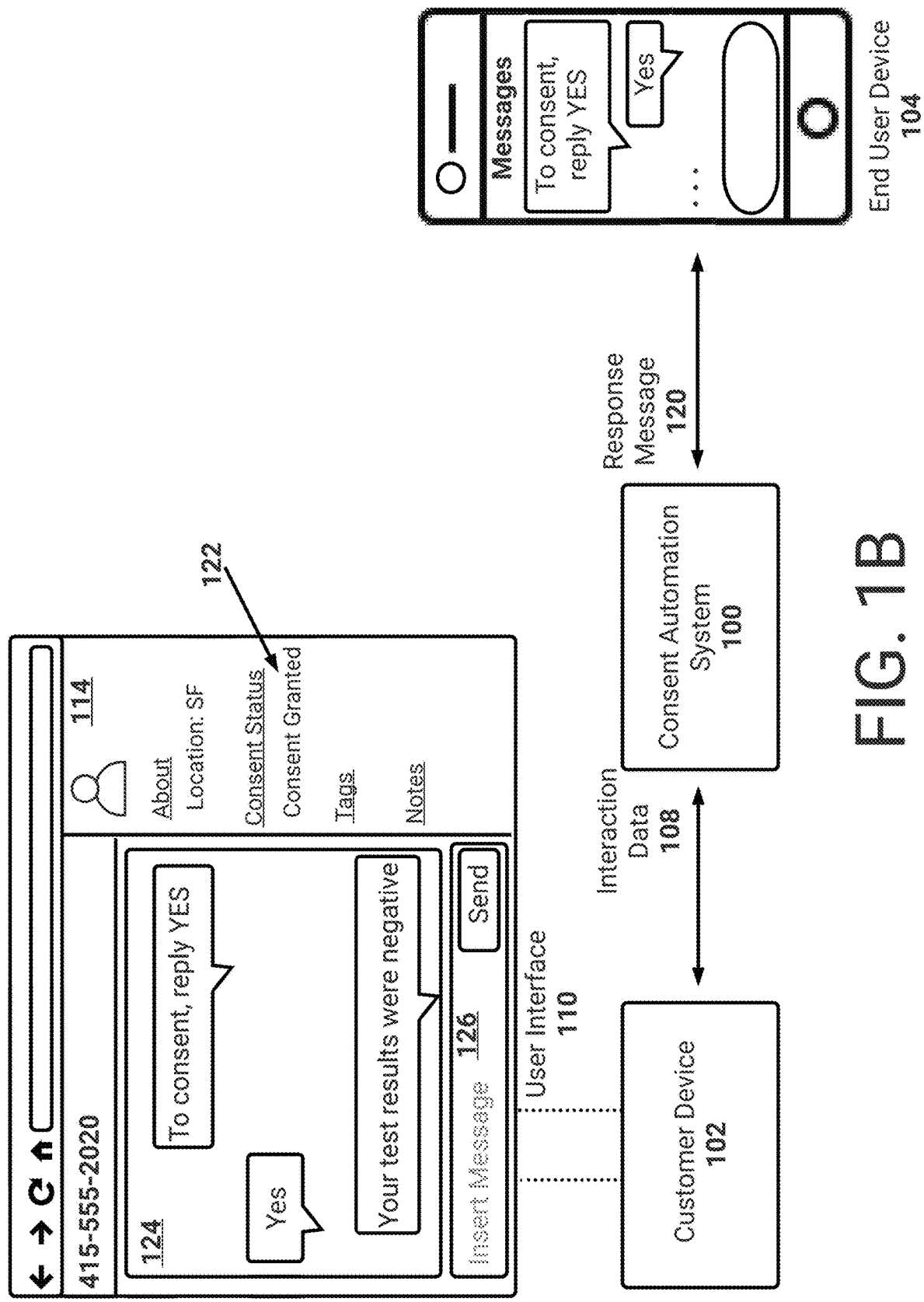
FIG. 1B illustrates a block diagram of the example consent automation system receiving a message including affirmative consent from the end user device.

FIG. 1B illustrates a block diagram of the example consent automation system 100 receiving a response message 120 indicating affirmative consent from the end user device 104. As described in FIG. 1A, an end user of the end user device 104 may respond to a received consent message 106. In the illustrated embodiment, the end user has provided a response message 120 identifying that the end user authorizes sensitive information to be directly messaged to the end user.

In some embodiments, the response message 120 may be provided to a phone number associated with the consent automation system 100. An outside system may receive response message 120 and provide it via a network (e.g., the internet) to the outside system 100 using an API. For example, the response message 120 may be provided via an HTTPS request. In some embodiments, the response message 120 may be obtained via software executing on the consent automation system 100.

The consent automation system 100 may therefore obtain the response message 120 and analyze the specified text to determine whether the end user authorizes use of direct messaging. In some embodiments, the user interface 110 may enable specification of a specific response message which is required to be entered by end users. For example, FIG. 1A illustrated a consent message 106 which specified that end users respond with 'YES.' The consent automation system 100 may therefore ensure that the text included in the response message 120 includes the specified text. As will be described, in some embodiments the consent automation system 100 may authorize further arbitrary communication with an end user if a response message includes text which is similar to a specific response message.

Based on the end user providing text indicating affirmative consent, the consent automation system 100 may update a consent state associated with the end user. For example, the consent automation system 100 may maintain, or be in communication with, one or more databases. In this example, the consent automation system 100 may update stored information to reflect the receipt of affirmative consent. The user interface 100 may then be updated by the consent automation system 100 to reflect the updated consent state. For example, FIG. 1B illustrates that the detailed information 114 indicates in portion 122 that consent has been granted.

In addition to reflecting that consent has been granted, the user interface 110 has additionally updated to enable arbitrary messaging of the end user. For example, the user interface 110 includes a chat window 124 which has been updated to depict a history of direct messages with the end user. In this example, the chat window 124 includes direct messages which have been provided to the end user and also received from the end user. The chat window 124 includes an input portion 126 in which the customer user may create a message. The input portion may be used by the customer user to specify sensitive information to be provided to the end user. As an example, the customer user may type text into the input portion. Example text may relate to medical information, such as text to inform the end user that his/her pharmaceutical is ready for pickup.

In some embodiments, the input portion 126 may allow for creation of messages which include additional elements as compared to textual messages. As an example, the customer user may select an option via the input portion 126 to attach an image. In this example, the input portion 126 may have a graphical element indicative of attaching an image. The customer user may select, or otherwise interact with, the graphical element. In response, the user interface 110 may update to enable selection of an image. For example, the user interface 110 may present images which are on the customer device 102. As another example, the user interface 110 may present images which are accessible via a network (e.g., the internet). In this example, the images may be associated with the end user in a database (e.g., cloud storage). Example images may relate to medical information of the end user and may, in some embodiments, be obtained from an electronic medical record system in communication with the consent automation system 100.

The input portion 126 may additionally allow for creation of messages with audio or video attachments. In embodiments in which the messages are MMS or SMS texts, these audio or video attachments may be down-sampled or otherwise reduced in size prior to receipt by the end user device 104. In some embodiments, a message which includes an audio or video attachment may be provided with a reference (e.g., a link) associated with the attachment. For example, a web address may be included in the message. The end user may select the web address to access (e.g., view, download, listen to) the attachment. In this example, the consent automation system 100 or an outside system (e.g., a secure system) may store the attachment. In some embodiments, the attachment may be stored temporarily and deleted upon access to the attachment.

Similarly, in some embodiments the input portion 126 may allow for creation of messages with file attachments. Example file attachments may include documents, spreadsheets, portable document format files, and so on. As an example, the customer user may attach test results in a document format. Certain types of direct messaging, such as via the rich communication service protocol, may allow for the above-described file attachments. Thus, the customer user may use the user interface 110 to attach arbitrary information for sending to the end user.

In the description of FIGS. 1A-1B, it may be appreciated that compliance with example regulations regarding sensitive information is inescapable. For example, in FIG. 1A the end user had not yet authorized receipt of sensitive information via direct messaging. As illustrated, the customer user had no ability to message the end user via the user interface 110 apart from requesting consent. The user interface 110 may utilized as a front-end interface of a web application or as a mobile application. Thus, an entity may have its employees use the user interface 110 when messaging, or otherwise contacting, end users. Since the user interface 110, and consent automation system 100, enforce consent, the entity can be assured that its customer users are following example regulations (e.g., HIPAA).

Additionally, in some embodiments the consent automation system 100 may maintain consent states for each of the end users. In this way, the consent automation system 100 may document times at which consent is either received or revoked from end users. Consent states may then be updated accordingly, such that current states are known. Furthermore, these consent states may be automatically updated by the consent automation system 100. For example, the consent automation system 100 may receive all messages from end users. These messages may be analyzed to ascertain whether the end users have provided affirmative consent. These messages may also be analyzed to ascertain whether the end users have revoked consent. In this way, the consent automation system 100 addresses technological problems associated with messaging tools. For example, prior messaging tools relied upon customer users to update whether end users have provided consent.

Based on the above-described documented consent, a customer user may be assured that if the customer user is able to create arbitrary messages (e.g., via input portion 126) then consent has been received.

Figure 2A:
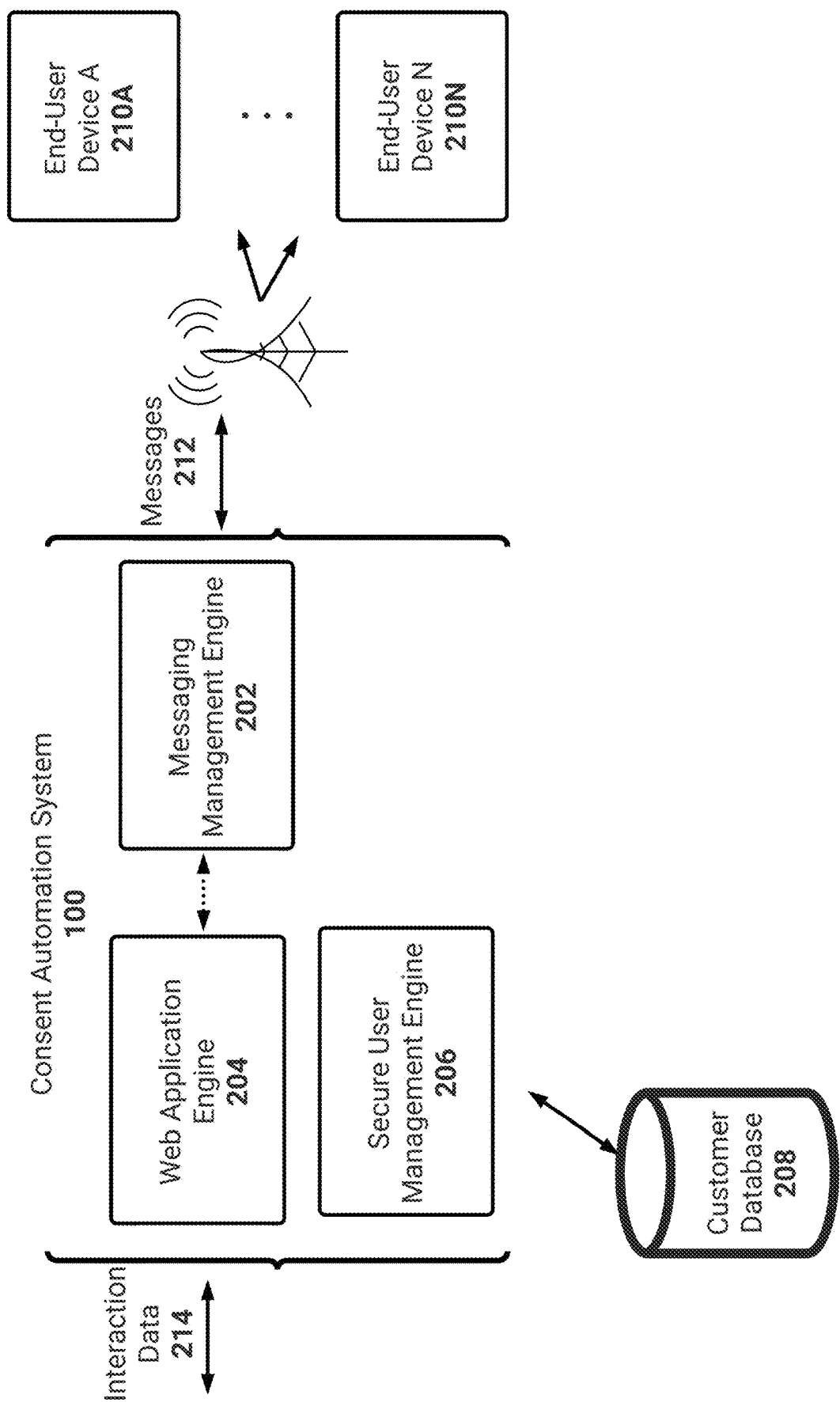
FIG. 2A illustrates a detailed block diagram of the example consent automation system.

FIG. 2A illustrates a detailed block diagram of the example consent automation system 100. The consent automation system 100 may, in some embodiments, represent an application or software which is executing on a system (e.g., a cloud system). For example, the consent automation system 100 may represent an application which is executing on a cloud platform. In some embodiments, the application may include disparate elements which collectively combine to enable the techniques described herein. These elements may, as an example, execute on different systems and may be in communication with each other using network calls.

In the illustrated example, the consent automation system 100 includes a messaging management engine 202. As described above, the consent automation system 100 may allow for customer users to provide direct messages to end users. Similarly, the consent automation system 100 may allow for end users to provide direct messages to customer users. In this example, the end users may provide messages to one or more phone numbers associated with the secure authorization system 100. Example messages from an end user may be provided to the system 100 in response to messages from the system 100 (e.g., arbitrary messages, consent messages). An example message from the end user may also be provided as an initial contact with the system 100 (e.g., a first touch with a phone number associated with an entity). For this example message, the system 100 may automatically provide a consent message to the end user. The messaging management engine 202 may orchestrate this messaging functionality. For example, the messaging management engine 202 may represent software (e.g., an application) which enables responding to, and providing, text messages via cellular networks.

While phone numbers are described above, in some embodiments messages may be provided to user names or email addresses. For example, an end user may be associated with a username or email address used by an application. In this example, direct messages may be provided to the username or email address via the application. Similarly, the system 100 may be responsive to messages provided to one or more usernames or email addresses associated with the system 100. In this way, end users may provide messages to customer users via the application. For example, the system 100 may execute the application or be routed messages from an outside system associated with the application.

The messaging management engine 202 may, as an example, be in communication with a third party system or application. For example, to transmit, or receive, a message the messaging management engine 202 may use an API associated with the third party system or application (e.g., via a REST API). As another example, the messaging management engine 202 may generate a network call. An example network call may include an HTTP POST message, in which the body includes information associated with the message to be sent. Example information may include information identifying an end user (e.g., a phone number), a body of the message (e.g., the text to be included), and so on.

The messaging management engine 202 may enable receipt of messages from end users via one or more phone numbers. For example, the messaging management engine 202 may allow for customer users to send messages from one or more phone numbers. In some embodiments, each customer user may be assigned a unique phone number. In some embodiments, groups of customer users may be assigned respective phone numbers. For example, a particular team of employees associated with an entity may utilize a same phone number. Similar to the above, a third party system or application may receive a message from an end user which is directed to one of the phone numbers and may route the message to the messaging management engine 202. For example, the engine 202 may receive information identifying the end user (e.g., a phone number), a body of the message, and so on. The phone number may be used to identify the specific end user as described herein. While the above focused on phone numbers, in some embodiments messaging may be associated with email addresses, usernames associated with a third party messaging application, and so on.

The consent automation system 100 further includes a web application engine 204. As described with respect to FIG. 1A, in some embodiments the secure authorization system 100 may implement a web application which is accessible by customer users via respective browsers. The web application engine 204 may therefore cause presentation of an interactive user interface, such as user interface 110, on user devices of the customer users.

The web application engine 204 may also trigger actions to be performed. For example, a customer user may provide user input (e.g., interaction data 214, which may be the same as interaction data 108) to the interactive user interface. The web application engine 204 may receive the user input, and cause performance of actions accordingly. For example, the customer user may provide a query or search string to cause searching of a particular end user. In response, the web application engine 204 may cause searching of a database (e.g., customer database 208) and update the interactive user interface with results. Similarly, the web application engine 204 may cause a message (e.g., a text message) to be provided to an end user. In this example, the web application engine 204 may provide information to the message management engine 202 or directly to a third party system or application.

Customer users may be associated with profile information (e.g., user accounts) with the web application engine 204. For example, a customer user may provide a username and password via the interactive user interface. The web application engine 204 may then update the user interface to present conversations in which the customer user has previously engaged. In some embodiments, the web application engine 204 may present conversations in which all customer users, or customer users associated with a same team or group, have engaged. For example, all conversations which are associated with a particular phone number may be presented. In this way, more than one customer user may continue, or initiate, messages with end users.

The consent automation system 100 further includes a secure user management engine 206, which may enable access to end user information stored in the customer database 208. In some embodiments, the customer database 208 may represent a database hosted by a cloud or online platform. For example, the customer database 208 may be in communication with the secure user management engine 206 via a network connection (e.g., an HTTPS connection). As another example, the customer database 208 may be an in-memory data structure, such as a Redis database. The secure user management engine 206 may enable storage, and retrieval, of information from the customer database 208. Additionally, the secure user management engine 206 may enable searching of the customer database 208. Example searching may include use of Elasticsearch, and so on. For example, a search query may be processed by the secure user management engine 206.

The customer database 208 may indicate personal information associated with end users. Example personal information may include the end user's name, phone number, username (e.g., for an application), email address, and so on. The customer database 208 may additionally store messaging histories associated with end users. For example, the customer database 208 may store the messaging history identified in portion 124 of FIG. 1B as being associated with a particular end user (e.g., the end user associated with phone number 112).

The customer database 208 may additionally store information identifying consent states associated with the end users. In this way, the secure user management engine 206 may rapidly identify whether any end user has responded to a consent message with an affirmative, negative, or with no, response, and with a history of state changes. The state change may therefore enable inescapable compliance, as the customer user's actions may be constrained based on the state. For example, and as described in FIGS. 1A-1B, a customer user may be unable to send arbitrary messages to an end user who has not yet provided affirmative consent.

The secure user management engine 206 may access the customer database 208 to identify end users associated with a particular entity. For example, the customer database 208 may allow for importing information (e.g., comma separated value files, arbitrary data files) which indicates end users associated with an entity. In this example, customer users of the entity may add end users which may then receive consent messages as described herein. The customer database 208 may therefore allow for mass, or otherwise large scale, importation of end users into the customer database 208. In some embodiments, newly included end users may be assigned consent states which identify that the end users have not yet provided affirmative consent. In some embodiments, the imported information may reflect consent states of the end users. For example, if an end user has previously responded with an affirmative response message, the customer database 208 may be updated to reflect this affirmative consent.

Without being constrained by way of example, it may be appreciated that the customer user may use the user interface 110 described in FIGS. 1A-1B to add end users. For example, the user interface 110 may enable adding additional end users via one or more input portions. In this example, the customer user may thus specify personal information for an end user. This received personal information may be provided via the secure user management engine 206 for storage, or inclusion, in the customer database 208. For example, the web application engine 204 may receive the personal information as interaction data 214 from the customer user. The web application engine 204 may then provide the personal information to the secure user management engine 206.

In some embodiments, the secure user management engine 206 may identify end users which may be duplicates in the customer database 208. For example, a customer user may specify an end user's phone number and name. In this example, the customer database 208 may include information identifying an end user with a same phone number but different name. In some embodiments, the secure user management engine 206 may determine a likelihood associated with the names corresponding to a same person. In this way, the likelihood may indicate whether the customer user incorrectly entered the end user's name. An example technique may include determining a distance metric between the names (e.g., a Levenshtein distance). In some embodiments, the secure user management engine 206 may use additional personal information such as the end user's address, email address, and so on. In this say, the secure user management engine 206 may determine that the name was entered incorrectly and may update the name accordingly. In some embodiments, the user interface 110 may be updated to reflect that a person with the same phone number has already been entered as an end user. The customer user may therefore update the entered name, confirm the name with the end user, and so on.

It may be appreciated that certain phone numbers may be re-used, such that two different end users may use the same phone number at different times. In some embodiments, the secure user management engine 206 may identify that a phone number is already stored in the customer database 208 as being associated with a first end user. A customer user who is entering personal information for a second end user may, as an example, be alerted that the phone number is existent in the customer database 208. Similar to the above, the secure user management engine 206 may determine a likelihood associated with the first end user and second end user corresponding to a same real-world person. For example, the likelihood may be based on a distance metric associated with the corresponding names, an address, and so on. Thus, the secure user management engine 206 may determine that the likelihood is below a threshold. In this way, the secure user management engine 206 may allow for entering of the phone number. Additionally, the secure user management engine 206 may update a consent state associated with the phone number such that the second end user is required to provide affirmative consent.

The consent automation system 100 may therefore enable messages 212 to be provided to end user devices 210A-210N. As described above, customer users may use a user interface to provide interaction data 214. In response, the consent automation system 100 may allow for a multitude of messages 212 to be provided to end user devices 210A-210N. These messages may include consent messages, arbitrary messages which include personal or sensitive information, and so on. In some embodiments, and as will be described in FIGS. 5 and 8A-8D, the consent automation system 100 may allow for a message to be announced (e.g., provided) to a multitude of end users at a same time. In these embodiments, the consent automation system 100 may ensure that only end users who have consented to such direct messaging may receive the message.

Figure 2B:
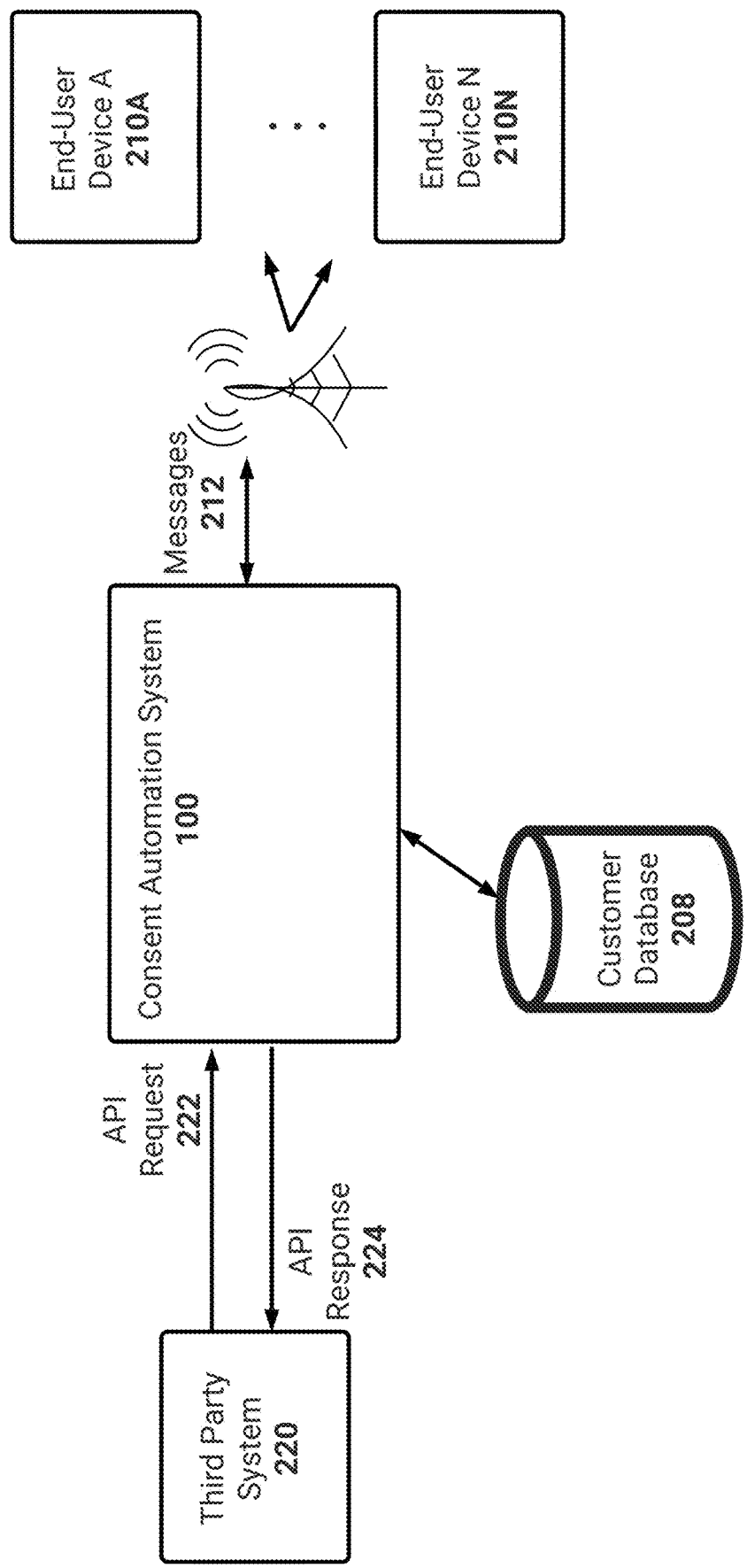
FIG. 2B illustrates another block diagram of the example consent automation system.

FIG. 2B illustrates another block diagram of the example consent automation system 100. In some embodiments, the consent automation system 100 may provide one or more application programming interfaces (APIs) to enable third-party systems to use the compliant messaging techniques described herein. For example, a third-party system may use the consent automation system 100 to ensure compliance with HIPAA or other privacy laws or regulations when providing medical information, such as protected health information. In some embodiments, a software development kit (SDK) may be utilized in third-party applications which enables communications with the consent automation system 100.

The consent automation system 100 may therefore respond to API requests received from third-party systems, such as via a network (e.g., the internet). Example API requests may include POST requests optionally with JavaScript Object Notation (JSON) responses. For example, an API request may include Example API requests, may further include representation state transfer (REST) requests, remote procedure call (RPC) requests, and so on. An example API request 222 may include transmitting a message to a particular end user. Another example API request 222 may include identifying a consent state for a particular end user. Another example API request 222 may include importing personal information associated with a multitude of end users, and so on. Another example API request 222 may include causing a mass communication to a multitude of end users, for example as described with respect to FIGS. 8A-8D.

The illustrated third party system 220 may represent a system which is associated with an application, software, and so on, for messaging or communications. For example, an entity may provide a messaging tool such as SLACK™, ZOOM™, a verbal personal intelligent assistant, and so on, to enable communications by customer users with end users. With respect to a video communication application (e.g., ZOOM), a medical professional may discuss medical information with a patient during a video call. The medical professional may additionally interact with the video communication application to cause a message to be directly provided via text (e.g., an SMS and/or MMS text message) to the patient through the API request 222.

Advantageously, the message may be provided to the consent automation system 100 via the API request 222. The message may reflect an intended patient (e.g., a name, a phone number, an email address), a body of the message (e.g., text, audio, video, images), and so on. Thus, the consent automation system 100 may access the customer database 208 and identify a consent state for the intended patient. The consent automation system 100 may determine that the patient has previously responded to a consent message with an affirmative response (e.g., 'YES'). Based on this determination, the consent automation system 100 may therefore route the message 212 to the patient's user device. In contrast, if the consent automation system 100 determines that no affirmative consent has been received for the patient, the consent automation system 100 may block transmission of the message. Instead, the consent automation system 100 may cause a consent message (e.g., consent message 106 in FIG. 1A) to be provided to the patient's end user device. Similarly, the medical professional may interact with the video communication application to cause the consent automation system 100 to identify whether the patient has consented to direct messaging of medical information.

The consent automation system 100 is illustrated as providing an API response 224 to the third party system 220. An example API response 224 may include identifying whether a message was provided to one or more end users (e.g., an 'Ack'). Another example API response 224 may include providing information identifying a consent state associated with an end user. For example, a customer user may utilize an application (e.g., SLACK™) to request that the consent automation system 100 identify a consent state for a specified end user. The consent automation system 100 can then access the customer database 208 and provide the API response 224 which indicates whether affirmative consent has been provided.

The illustrated embodiment includes the consent automation system 100 providing message 212 to one or more end user devices 210A-210N. Thus, the consent automation system 100 may allow for customer users to leverage the enhanced messaging techniques described herein while maintaining their preferred workflow which leverages different third party systems, applications, and so on.

Example Flowcharts

FIG. 3A is a flowchart of an example process 300 for enforcing compliance based on consent messages as described herein. For convenience, the process 300 will be described as being performed by a system of one or more computers (e.g., the consent automation system 100).

At block 302, the system causes presentation of an interactive user interface. As described with respect to FIGS. 1A-1B, a customer user associated with an entity may leverage a user interface to provide messages to end users. For example, the user interface may be associated with a digital messaging tool. The user interface may be provided, for example as web information, for rendering on a user device of the customer user. The user interface may also be presented via an application executing the user device and the system may provide information for inclusion in the user interface.

The customer user may, as an example, have a user account with the system, such as a username and password. Upon access to the user interface, the user interface may update to reflect conversations or messages in which the customer user has previously engaged. In some embodiments, the user interface may reflect conversations in which any customer user associated with the entity, or any customer user associated with a same team, has previously engaged.

At block 304, the system responds to selection of a particular end user. The customer user may provide user input to the user interface to select the particular end user. For example, the user input may include touch input, voice input, keyboard/mouse input, and so on. The system may allow for the end user to search for a specific end user via entering a search query. The system may also present a list, or identification of end users which have been entered into the system.

At block 306, the system accesses consent state information for the selected end user. The system may maintain consent states for each end user who is reflected in stored information accessible to the system. In some embodiments, the system may assign each end user an initial state indicating that the end user has not providing affirmative consent. As described above, the system may update the consent state information for a user based on the user providing affirmative consent. For this example, the system may update the consent state information to indicate affirmative consent was received. The system may also update the consent information for a user based on the user providing a message indicating that they revoke consent. For this example, the system may update the consent state information to indicate receipt of refusal of consent.

The system determines whether affirmative consent has been received from the selected end user, and if no consent has been received then at block 308 the system constrains actions available to the customer user. If the customer user is using an interactive user interface associated with the system, such as illustrated in FIGS. 1A-1B, the system may limit actions which are available for selection by the user. For example, the system may update the user interface to include a selectable option associated with sending a consent message to a phone number associated with the end user.

If the customer user is using a third party application or system, such as described with respect to FIG. 2B, the system may disallow sending of arbitrary messages to the customer user. For example, the system may provide information to the customer user indicating that the customer user is only able to send a consent message. As another example, the system may automatically transmit a consent message to the end user and discard a message entered by the customer user.

If the system determines that consent has been received, then at block 310 the system allows for arbitrary messaging of the selected end user. For example, if the custom user is using the interactive user interface associated with the system, the customer user may include arbitrary text, images, video, and so on. In this example, the user interface may include an input portion to allow for the messaging. As another example, if the customer user is using a third party application or system, the system may route arbitrary messages to the end user. For example, the system may provide the messages as text messages to the end user.

FIG. 3B is a flowchart of a process 320 which further describes the example process 300 for transmitting arbitrary messages to an end user. For convenience, the process 320 will be described as being performed by a system of one or more computers (e.g., the consent automation system 100).

At block 322, the system updates a user interface to reflect affirmative consent was received. As described for block 310, if the system stores information identifying that affirmative consent was received, the system may update the user interface to allow for arbitrary messaging.

At block 324, the system receives information to be provided to the selected end user. The user interface may include an input portion to allow for entry of arbitrary text.

At block 326, the system causes transmission of a message to the end user. The system may transmit the entered arbitrary text to an end user device associated with the end user. For example, the system may cause a text message to be provided to a phone number associated with the end user. In some embodiments, the system may cause a direct message to be provided to an application utilized by the end user. In these embodiments, the end user may be associated with a username, email address, and so on.

FIG. 3C is a flowchart of another example process 330 for automatically transmitting consent messages to enforce compliance. For convenience, the process 330 will be described as being performed by a system of one or more computers (e.g., the consent automation system 100).

At block 332, the system receives a message from an end user. The end user may have had previous interactions with the customer system, or the message may be the first communication between the end user and the customer system. The system may receive the message from a phone number which has not yet been provided a direct message by a customer user. In some embodiments, the system may receive the message from a username or email address (e.g., via an application). Thus, the end user may effectuate first contact with an entity (e.g., a pharmacy, medical professional's office, hospital, financial planner, and so on). As will be described, the system may ensure that consent is confirmed for this end user prior to customer users of the entity being allowed to provide arbitrary messages, either as responses to the end user-initiated communication or as subsequent customer user-initiated communications to the same user.

The entity (customer) may provide phone numbers at which end users can contact the entity. For example, a website of the entity may identify one or more phone numbers and indicate that end users can reach employees of the entity by messaging (e.g., texting) the phone numbers. As another example, a business card, sign, poster, and so on, may include one or more phone numbers of the entity. Thus, the end user may provide a message to a phone number of the entity which is associated with the system.

At block 334, the system accesses or creates identifying information associated with the end user. The end user may represent an end user who is known to the entity, such that identifying information for the end user is already stored by the system (e.g., in customer database 208 described above). For example, a customer user of the entity may have entered the phone number (or email address or username) for the end user along with identifying information. In this example, the end user may have interacted with the entity in the past (e.g., visited a pharmacy, spoken with a medical professional, and so on). The system may therefore access identifying information for this end user based on the phone number associated with the received message. Thus, the system may access the identifying information even if messages have not been previously sent to the end user. Example identifying information may include a name, address, and so on as described herein.

The end user may also represent an end user who is unknown to the entity. For example, the end user may have been walking on a street and noticed a sign (e.g., advertisement) for the entity. Subsequently, the end user may have messaged a phone number included on the sign which is associated with the system. Thus, the end user's message described in block 332 may be routed to the system. The system may therefore create identifying information for the end user. For example, the system may update the customer database 208 to include the end user's phone number. The phone number may be the sole identifying information for the end user in this case, or the system may obtain other identifying information on the end user from public resources based upon the phone number.

At block 336, the system accesses consent state information for the end user. In the case that the end user has not been messaged by customer users of the entity before, the consent state for the end user may reflect that consent has not been received. As described herein, a default state for an end user may indicate that consent has not been received.

In some embodiments, a sign or website of the entity may request that an end user's initial message to the entity include particular text indicative of authorization to receive direct text messages from the entity. For example, the end user may provide a text with example text, "I consent to receiving text messages." In these embodiments, the system may set a consent state for the end user to reflect that consent has been received.

At block 338, if the consent state indicates that consent has not been received, the system may automatically transmit a standardized consent message to the phone number (or username or email address) associated with the received message. The end user may then respond to the consent message indicating affirmative consent, and the end user's consent state may be updated as described herein.

The system may additionally constrain actions of customer users. For example, the system may update a user interface utilized by one or more customer users to disallow arbitrary messaging to the end user. As another example with respect to third-party applications or systems, the system may disallow transmission of arbitrary messages to the end user. Instead, the system may only allow for sending of the standardized consent message to the phone number associated with the received message.

At block 340, if the consent state indicates that consent was received, the system allows arbitrary messaging of the end user. For example, the system may allow for arbitrary text messages to be provided to the phone number (or username or email address) associated with the received message.

Figure 4:
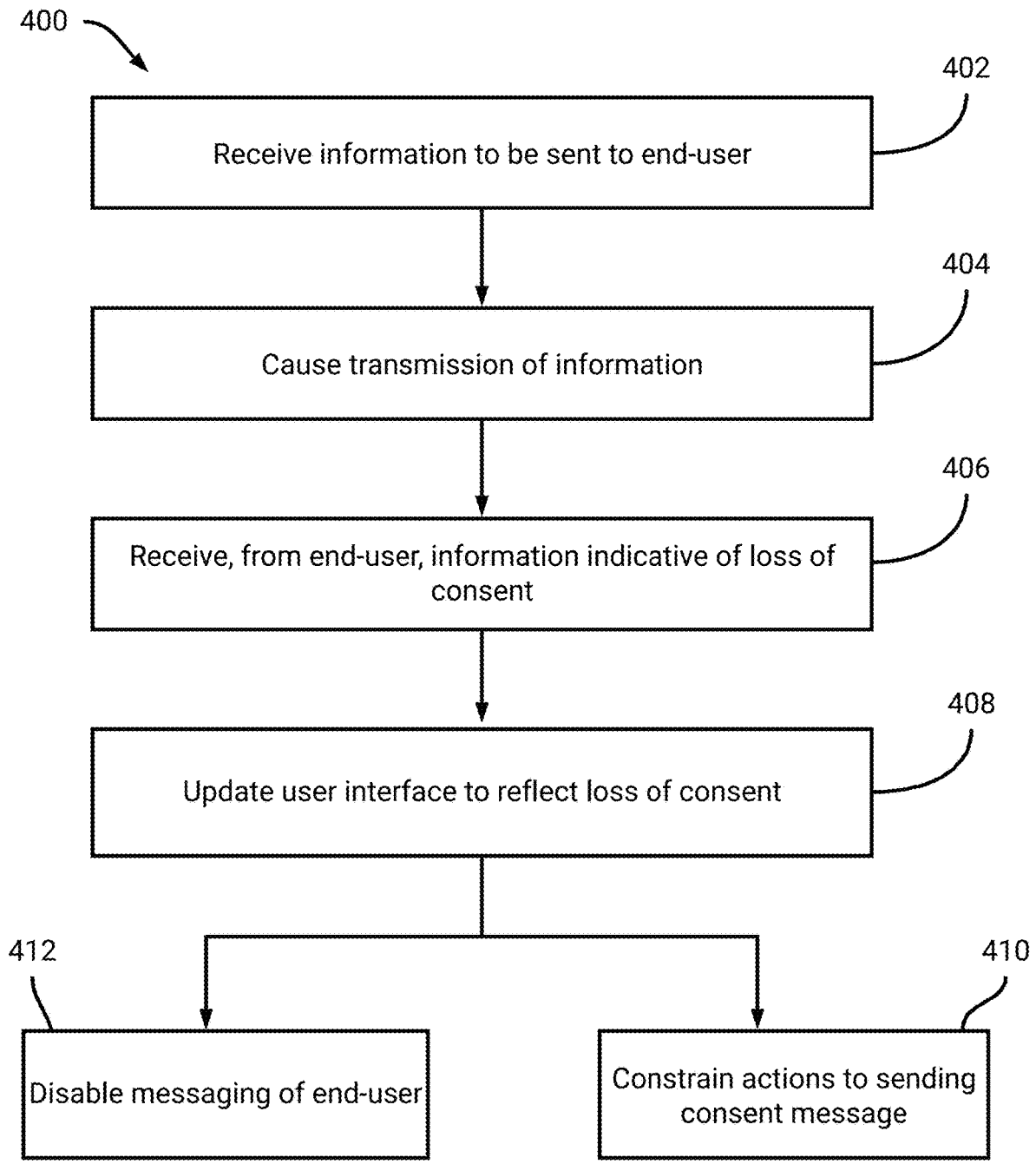
FIG. 4 is a flowchart of an example process for updating a user interface to reflect loss of affirmative consent from an end user.

FIG. 4 is a flowchart of an example process 400 for updating a user interface to reflect loss of affirmative consent from an end user. For convenience, the process 400 will be described as being performed by a system of one or more computers (e.g., the consent automation system 100).

At block 402, the system receives information to be sent to an end user. As described above, a user interface may be presented on a device used by a customer user. The customer user may then select the end user, and if affirmative consent has been received for the end user, the customer user may provide information to be sent to the end user. Example information may include textual information, images, video, audio, files, and so on. Additionally, the customer user may use a third party system or application and enter text to be provided to the end user.

At block 404, the system causes transmission of the information. As described above, the system may cause the received information to be sent to the end user. For example, the system may cause a text message to be transmitted to the end user.

At block 406, the system receives information indicative of loss of consent from the end user. The end user may provide a message, such as a text message, to the system indicating loss of consent. For example, the end user may provide the message to a phone number (or username or email address) associated with the system. As described above the system may use one or more phone numbers to send, and receive, messages. The end user may thus provide a message indicative of loss of consent. For example, in some embodiments the end user may provide a message identifying 'STOP' or a synonym thereof. As another example, the end user may receive information identifying terms or phrases which will cause loss of consent. This information may be included in a consent message previously provided to the end user. In some embodiments, and as described above, a deep learning model may be used to characterize text included in the received information.

In some embodiments, the system may periodically provide a message to the end user identifying that the end user can revoke affirmative consent, and how to effectuate such revocation. The end user can therefore be assured of an easy technique to disallow transmission of sensitive information via direct messaging, such as text messaging.

In some embodiments, the end user may indicate loss of consent using other techniques. For example, the system may be associated with an automated phone number which the end user may call. The end user may then indicate loss of consent via interaction with an automated phone call. As another example, the system may allow for end users to indicate loss of consent using a particular website. For this example, the end user may enter his/her phone number and indicate loss of consent.

At block 408, the system updates the user interface to reflect loss of consent. The system may update the user interface, such as the user interface of FIGS. 1A-1B, to reflect that the end user has revoked consent. For example, the system may present information identifying the consent state of the end user (e.g., in portion 114 of FIGS. 1A-1B). As another example, the system may remove an input portion 126 which allows for arbitrary messaging. Similarly, if the customer user is using a third party application or system the system may cause information to be presented to the user. As an example, a third party application may present information to the customer user identifying revocation of consent.

At block 410, the system may, in some embodiments, constrain actions to include transmitting a consent message. The system may allow for the customer user to transmit a consent message as described herein. For example, the system may allow the customer user to send a consent message to the end user. In this example, the system may limit a frequency or extent to which the end user can be messaged. For example, the system may allow a consent message to be provided every threshold amount of time (e.g., every day, every week, and so on).

At block 412, the system may, in some embodiments, disable messaging to the end-user. In some embodiments, the system may update the user interface to remove all functionality associated with messaging the end user. In this way, the customer user may be unable to transmit any message, including a consent message, to the end user, in response to a revocation 406 of previously granted consent. Similarly, if the customer user is using a third party application or system, the system may disallow messaging of the end user. For example, the system may discard messages received from the customer user.

In some embodiments, the end user may provide a text to identify affirmative consent again. For example, the end user may provide a text which includes "START." In this example, the system may re-allow arbitrary messaging to the end user, or may allow or sending of a standardized consent message to the end user as described herein. With respect to a standardized consent message, the end user may thus be required to indicate affirmative consent in a response message.

Figure 5:
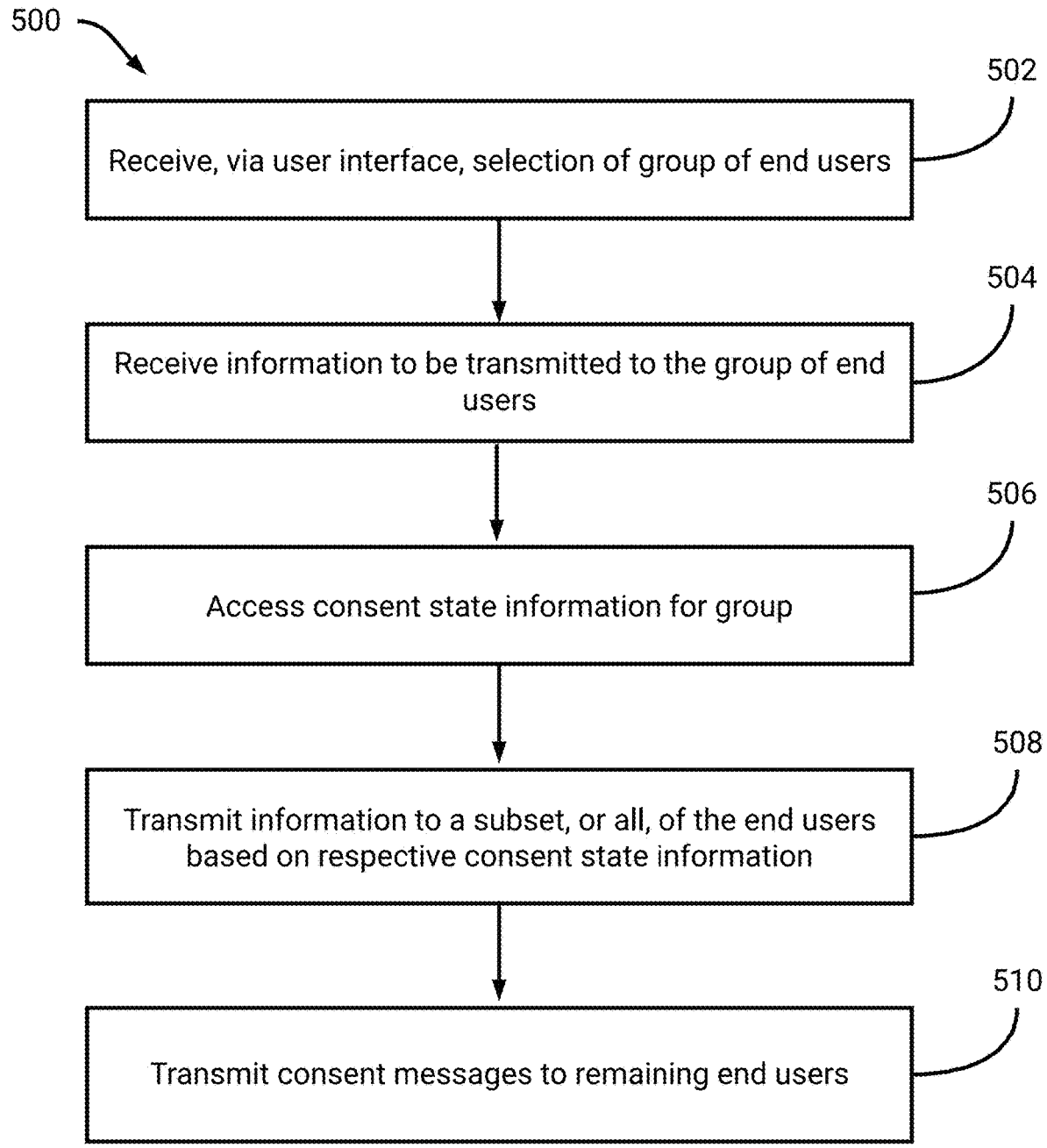
FIG. 5 is a flowchart of an example process for providing messages to a multitude of end users.

FIG. 5 is a flowchart of an example process 500 for providing messages to a multitude of end users. For convenience, the process 500 will be described as being performed by a system of one or more computers (e.g., the consent automation system 100).

At block 502, the system receives selection of a group of end users. A customer user may use a user interface, such as the user interfaces described with respect to FIGS. 1A-1B, to select a multitude of users. As an example, the user interface may allow for selection of visual elements proximate to a list or identification of users (e.g., checkboxes may be selected). The customer user may therefore interact with the visual elements to identify the group of end users.

In some embodiments, end users may be associated with labels which are usable to classify or characterize end users. These labels may be provided by customer users and stored by the system. For example, a medical professional may assign a label to end users which is related to a particular type of pharmaceutical. In this example, the medical professional can therefore identify that all end users assigned the label are to be included in the group.

At block 504, the system receives information to be transmitted to group of end users. The customer user may specify information including text, images, audio, video, and so on as described herein. This information may be specified using a user interface associated with the system (e.g., the user interface described in FIGS. 1A-1B). The information may also be specified using a third party application or system in communication with the system.

At block 506, the system accesses consent information for the group. The system accesses stored information reflecting consent states for each end user included in the group.

At block 508, the system transmits information to a subset, or all, of the end users. Each end user who has provided affirmative consent may be provided a message, such as a text message, which reflects the received information.

At block 510, the system may, as an example, transmit consent messages to remaining end users. The system may automatically provide consent messages to end users who have not provided affirmative consent. A particular remaining end user may therefore provide affirmative consent (e.g., provide a text message including 'YES'). In some embodiments, the system may queue a message for transmission to the remaining end users. In these embodiments, the particular remaining end users may thus receive the message upon providing affirmative consent. In some embodiments, the consent message may be customized to indicate that the end users have messages which are waiting to be transmitted, or may be even further customized to indicate the nature of the messages to be transmitted (without disclosing private information). In this way, the end users may identify that specific information for them is available.

The description above focused on providing an announcement to a multitude of users. In some embodiments, the system may allow for sending mass consent messages to the end users. Thus, a customer user may select a multitude of end users and the system may provide consent messages to these users. The system may then update consent states associated with the end users based on received responses. Non-limiting examples of such mass messages may relate, for example, to recall of or newly available generic substitutes for particular pharmaceuticals associated with the group.

Figure 6:
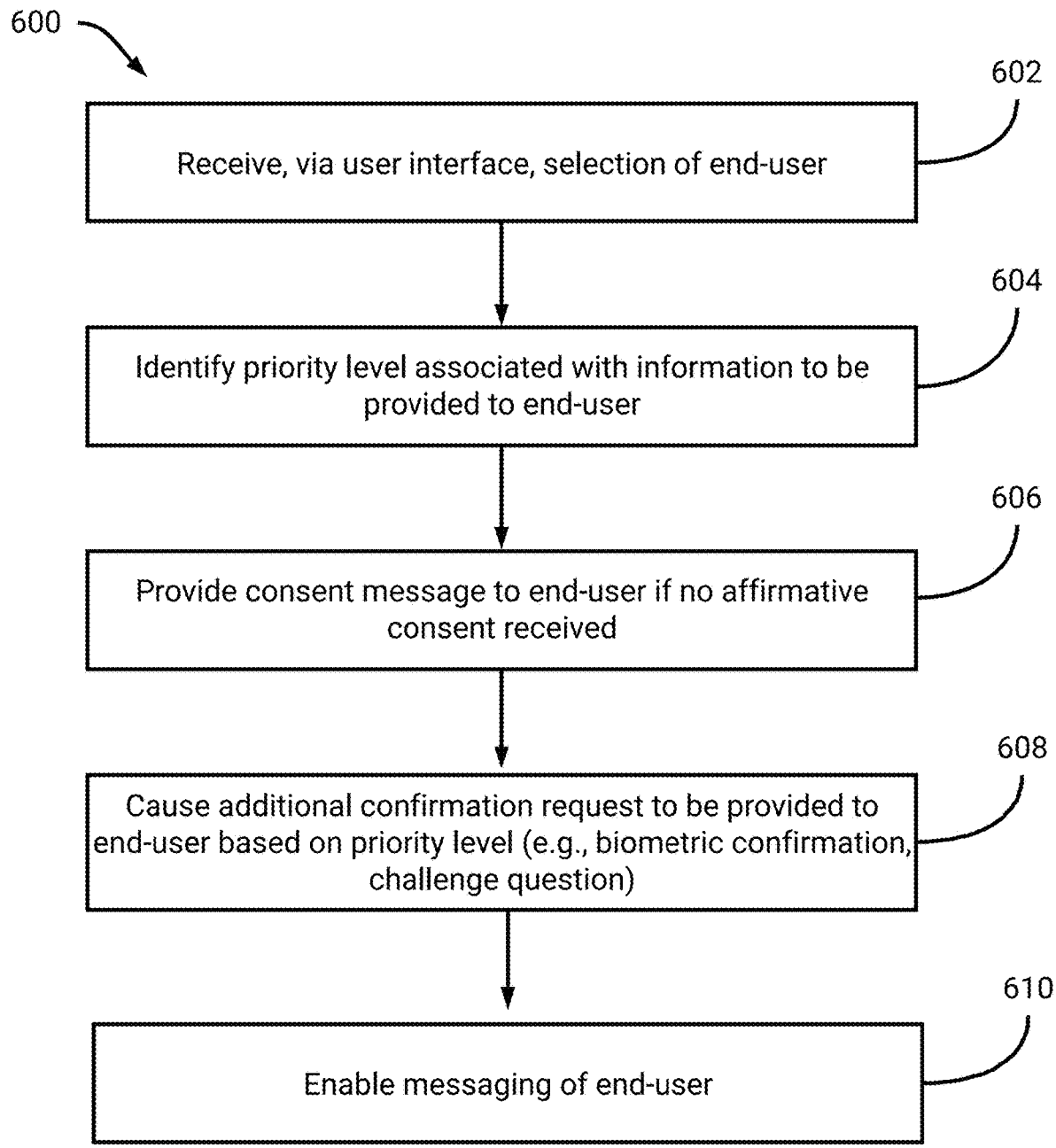
FIG. 6 is a flowchart of an example process for enforcing compliance based on consent messages and priority information.

FIG. 6 is a flowchart of an example process 600 for enforcing compliance based on consent messages and priority information. For convenience, the process 600 will be described as being performed by a system of one or more computers (e.g., the consent automation system 100).

At block 602, the system receives selection of an end user and at block 604 the system receives a priority level associated with information to be provided to the end user. A customer user may specify information indicative of a priority level. For example, a user interface used by the customer user may allow for a selection of a priority level from a multitude of priority levels. As another example, the priority level may reflect an importance which may be assigned. For example, messages may be assigned a nominal importance. In this example, the customer user may specify that a message to be sent to the end user is of a greater importance.

At block 606, the system provides a consent message to the end user if no consent has been received. The system identifies a consent state for the end user, and if no affirmative consent has been received, the system provides a standardized consent message to the end user as described herein.

At block 608, the system causes an additional confirmation request to be provided to the end user based on the priority level. For example, since the messages described herein may be provided as insecure text messages, the system may provide a challenge question to the end user. The specific additional confirmation request may depend on the priority level. For example, a higher priority level may require more complex challenge questions and/or may require biometric confirmation.

In some embodiments, the challenge question may be specified by a customer user based on stored information regarding the end user. As an example, a doctor may request that the end user identify that the end user provide information which would be unknown to other persons. In some embodiments, the system may access information associated with the end user and generate a challenge question. In some embodiments, the challenge question and accessed information may not include protected health information. An example challenge question may therefore not include specific identifying information associated with the end user and may instead relate to features of the end users (e.g., 'What, if any, medical procedure did you receive last year').

In some embodiments, the system may request biometric confirmation. For example, the system may be in communication with an application executing on a user device utilized by the end user. Example biometric confirmation may include confirmation of the end user's face, thumbprint, fingerprint, voice signature, and so on. The application maybe known to be associated with a phone number used by the user device of the end user. The application may thus provide confirmation information to the system which confirms an identity of the end user. In some embodiments, the application may output an alphanumeric code which the end user may provide to the system. For example, the end user may provide the code in a message to be transmitted to a phone number associated with the system.

At block 610, the system enables messaging of the end user. Based on receipt of affirmative consent and correct responses to the challenge request, the system may allow for messaging of the end user.

Example User Interfaces

FIGS. 7A-9C and 11A-1D illustrate example user interfaces which may be used by customer users associated with an entity. The user interfaces may be presented via a browser executing on a user device of a customer user. The user interfaces may also be presented by software or an application executing on the user device of the customer user.

Figure 7A:
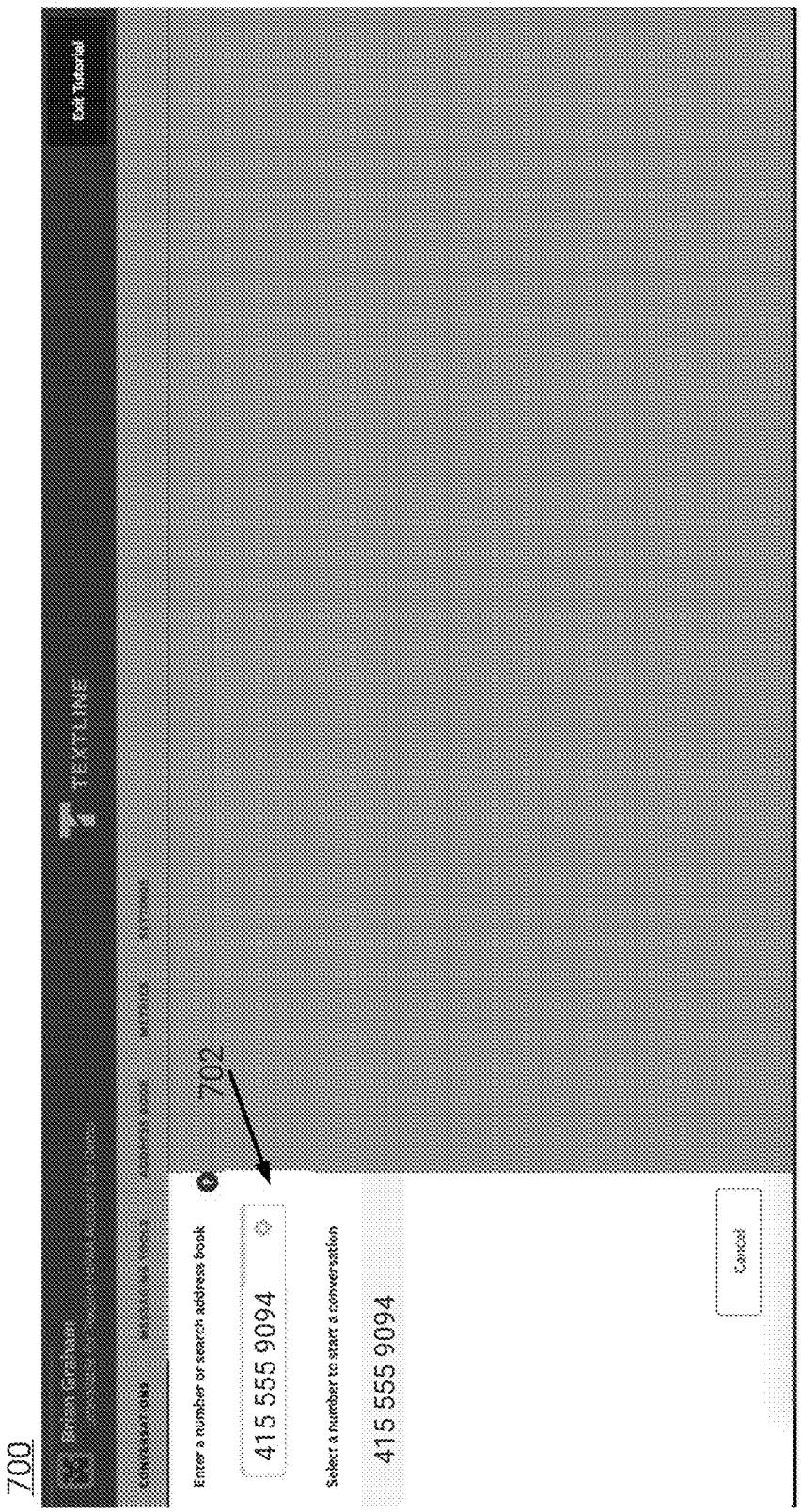
FIG. 7A is an example user interface illustrating identification of an end user who is to be messaged.

FIG. 7A is an example user interface 700 illustrating identification of an end user who is to be messaged. FIG. 7A includes an input portion 702 usable to specify information identifying an end user. The information may include a phone number of the end user. The information may also include a name of the end user.

In some embodiments, the input portion 702 may allow for specification of a query usable to identify the end user. For example, a customer user may specify features of the end user. The features may, as an example, be stored by the consent automation system 100. For example, an entity may have the features of end users they prefer to contact. These features may be uploaded or otherwise provided to the system 100. In some embodiments, identifying a specific end user based on features may be performed locally on a user device of the customer user. For example, locally stored information may be accessed and used to identify a phone number or name of the end user. In this way, the customer user may search for an end user who has recently purchased a particular pharmaceutical without the system 100 having access to that information.

Figure 7B:
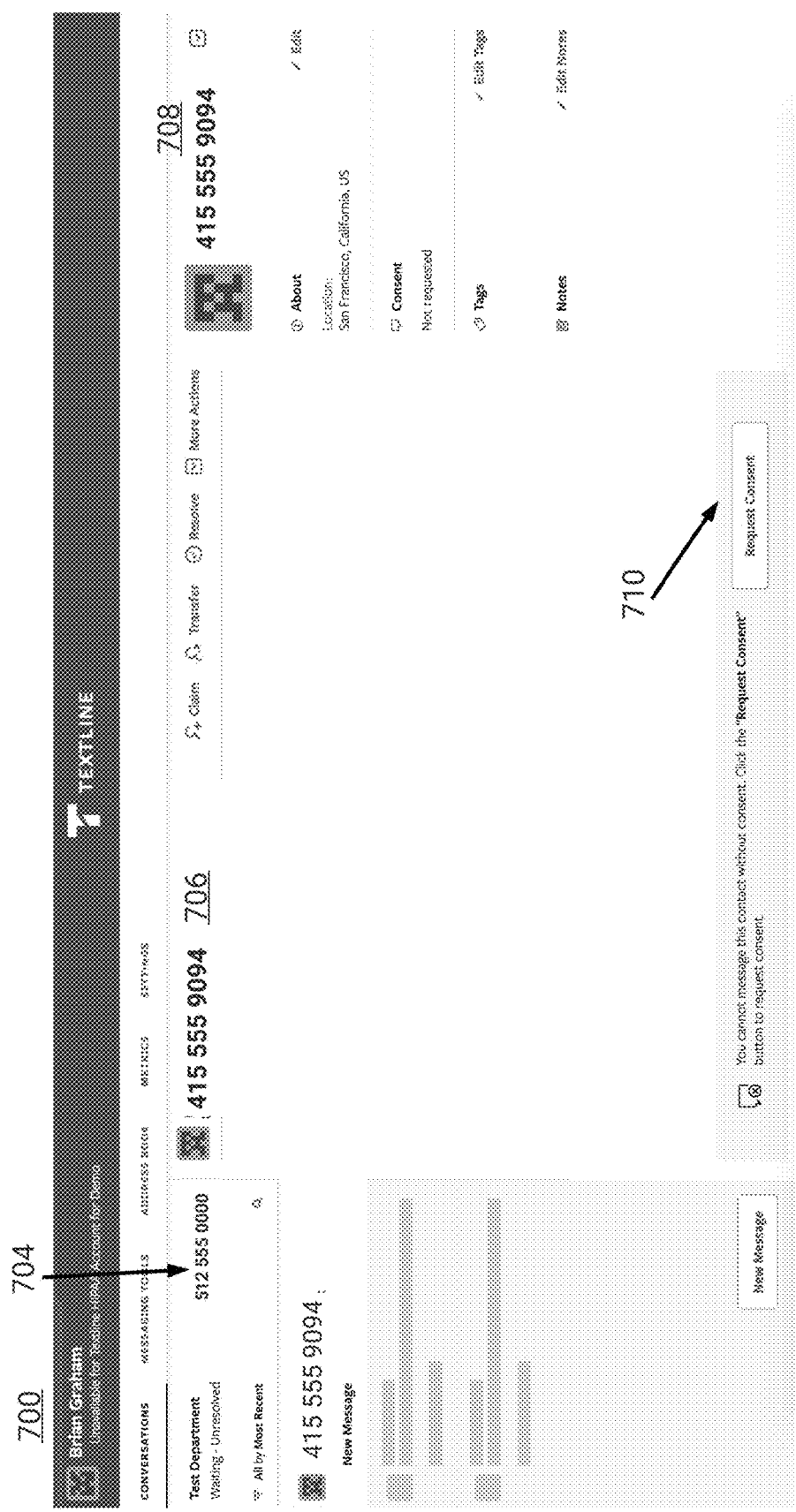
FIG. 7B is an example user interface illustrating a selectable option to provide consent messages.

FIG. 7B is an example user interface 700 illustrating a selectable option 710 to provide consent messages. Upon selection of an end user, the user interface 700 has updated to allow for sending of consent messages to the end user. As illustrated, the user interface 700 identifies a phone number which will be used to send messages to the end user in portion 704. The consent automation system 100 may allow an entity to use one or more phone numbers to transmit, and receive, messages. In some embodiments, each customer user may have his/her own phone number. In some embodiments, the phone number used may vary for the customer user.

The user interface 700 additionally includes chat window 706 which may present a chat history with the end user. In some embodiments, the chat history may reflect a chat history using a certain phone number 704. In some embodiments, the chat history may reflect a chat history using any phone number associated with the entity.

The user interface 700 further includes detailed information 708 for the end user. Example detailed information 708 includes a consent state for the end user, which in the illustrated example indicates that affirmative consent has not been received, and in the example has not been requested. Thus, the customer user is restricted to interacting with the selectable option 710.

Figure 7C:
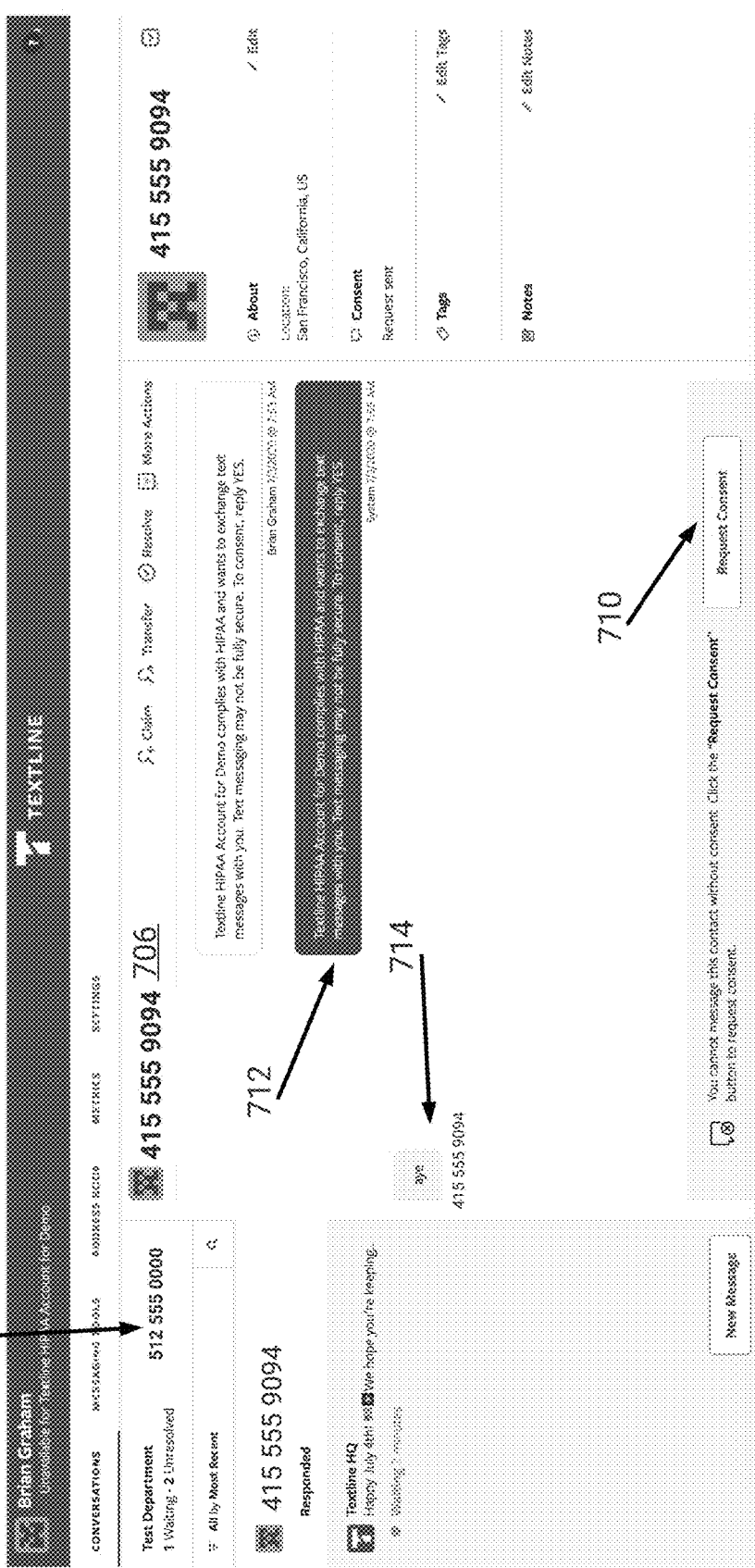
FIG. 7C is an example user interface illustrating receipt of an incorrect response message and maintaining the selectable option.

FIG. 7C is an example user interface 70 illustrating receipt of an incorrect response message 714 and maintaining the selectable option 710. In the illustrated example, the customer user has provided a consent message 712 which is reflected in the chat window 706. In response, the end user has provided a response message 714 from his/her user device. For example, the end user has used his/her mobile device to text the response message 714 to the customer phone number 704.

The provided response message 714 includes the text, "AYE." As identified in the consent message 712, the end user is required to respond with "YES." Thus, the consent automation system 100 may not update the consent state for the end user. As illustrated, the selectable option 710 remains in the user interface 700. In some embodiments, the consent automation system 100 may only update the consent state if the response message 714 includes the exact terms or phrase required in the consent message 712. Thus, if the response message included the following text, "YES AYE," the system 100 may not update the consent state for the end user.

Figure 7D:
FIG. 7D is an example user interface illustrating receipt of an affirmative consent response message.

FIG. 7D is an example user interface 700 illustrating receipt of an affirmative consent response message 716. As illustrated, the end user has provided a message 716 with the required text, "YES." In some embodiments, the system 100 may ignore case sensitivity. The system 100 has then automatically provided message 718 to indicate further information. The user interface 700 has additionally updated to reflect that the customer user can enter arbitrary information. For example, input portion 720 is now accessible to the customer user. Additionally, the detailed information 708 has updated to reflect the updated consent state for the end user. The updated consent state has been recorded at a particular time (e.g., '7/3/2020 @ 7:56 am'). In this way, the system 100 may store precise times at which consent was authorized.

Figure 7E:
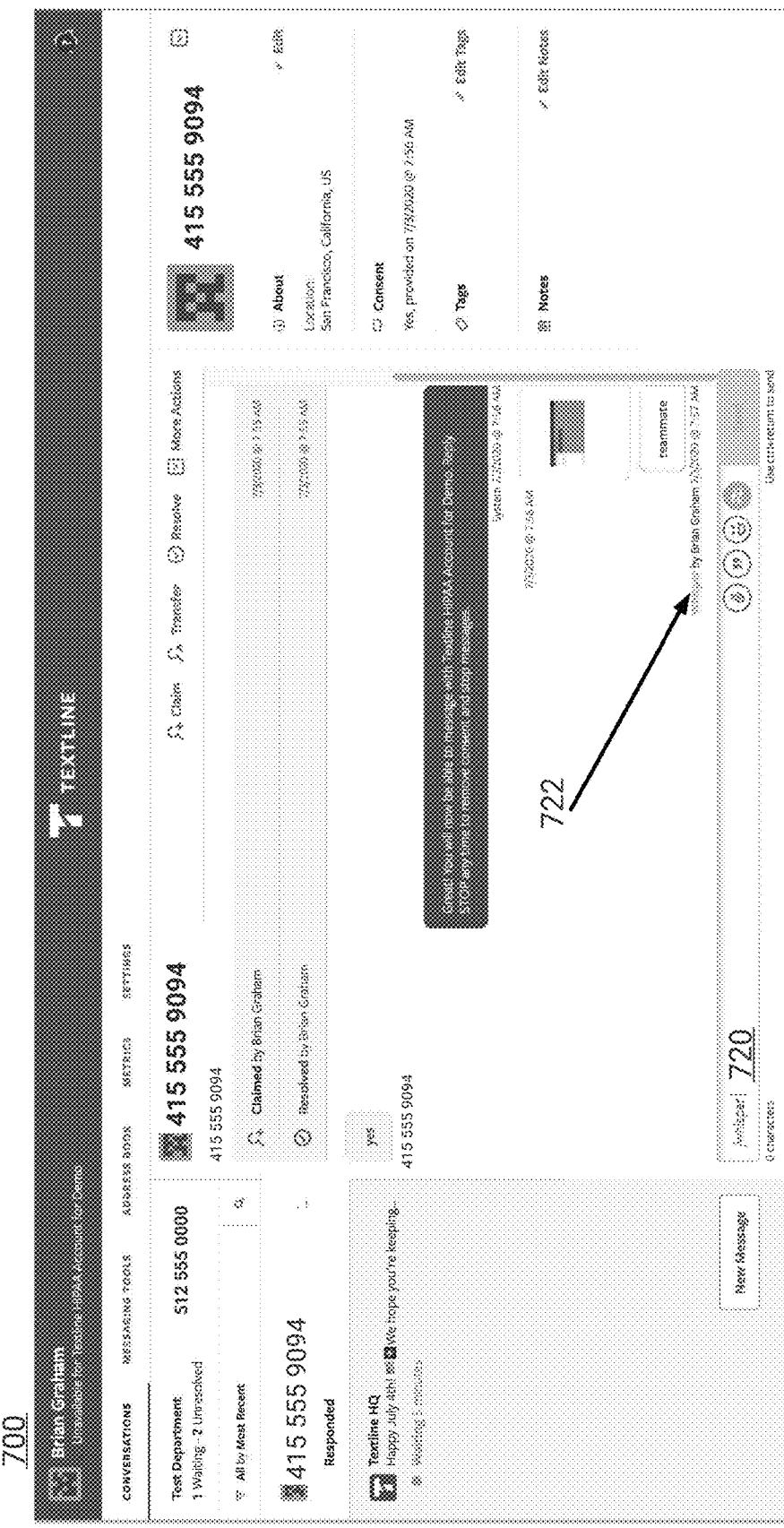
FIG. 7E is an example user interface illustrating a whisper message used for communications between customer users.

FIG. 7E is an example user interface illustrating a whisper message 722 used for communications between customer users. The customer user may provide information to other customer users associated with a same entity. For example, the customer user may specify certain text (e.g., '/whisper') in the input portion 720, or select a certain user interface option, to provide a message to other customer users. This message may be accessible to the other customer users using user interface 700. In this way, customer users for a same entity may communicate with each other in the chat window used to communicate with an end user. For example, the customer users may discuss aspects associated with the end user in the chat window with the discussion being hidden from the end user.

Figure 8A:
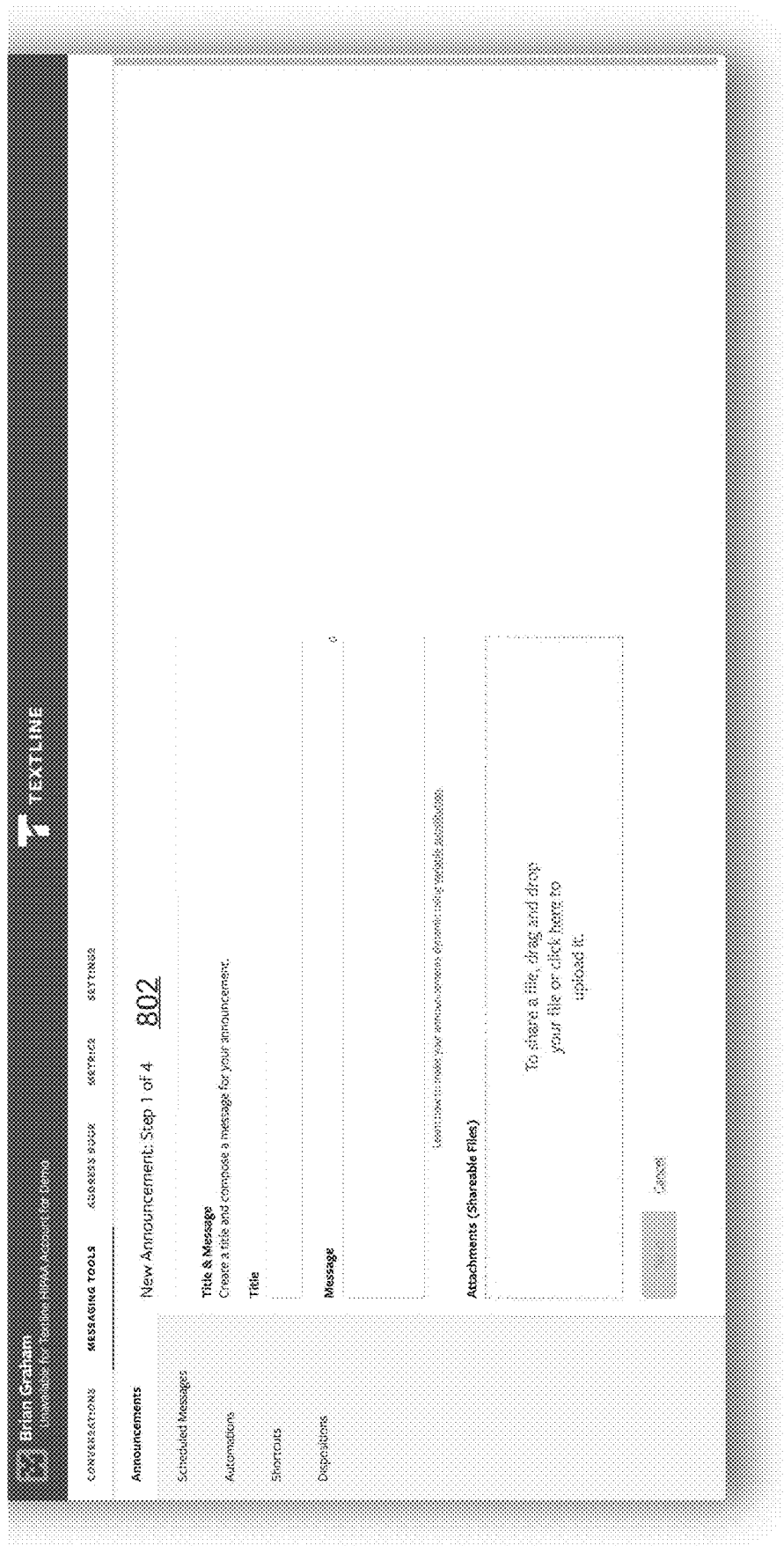
FIGS. 8A-8D are example user interfaces illustrating preparation of an announcement to one or more end users.

FIGS. 8A-8D are example user interfaces illustrating preparation of an announcement to one or more end users. FIG. 8A illustrates an example user interface 800 for providing an announcement to end users. The user interface 800 includes a first portion 802 which allows for specification of information to be used in the announcement. Example information includes a title, message, and/or attachments.

Figure 8B:
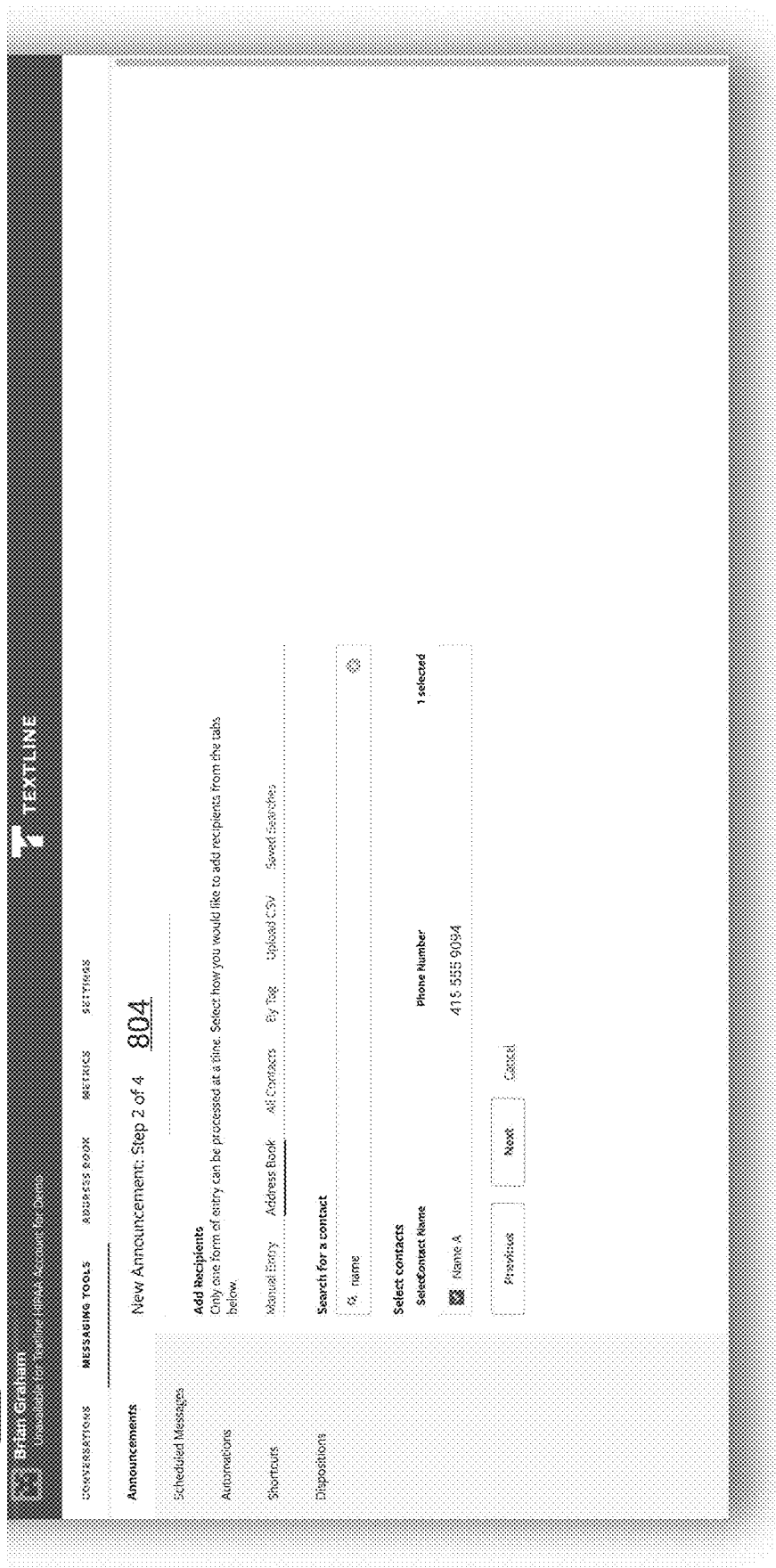

FIG. 8B illustrates the user interface 800 as including a second portion 804. The second portion 804 may allow for selection of end users to receive the announcement. As illustrated a particular end user has been selected (e.g., 'Name A'). The second portion 804 allows for searching of contacts according to name, phone number, or other identifying information or features. In some embodiments, the user interface 800 may identify whether the end users have provided affirmative consent. For example, the user interface 800 may include textual information, or graphical information (e.g., a graphical symbol), proximate to each end user indicating a consent state.

Figure 8C:
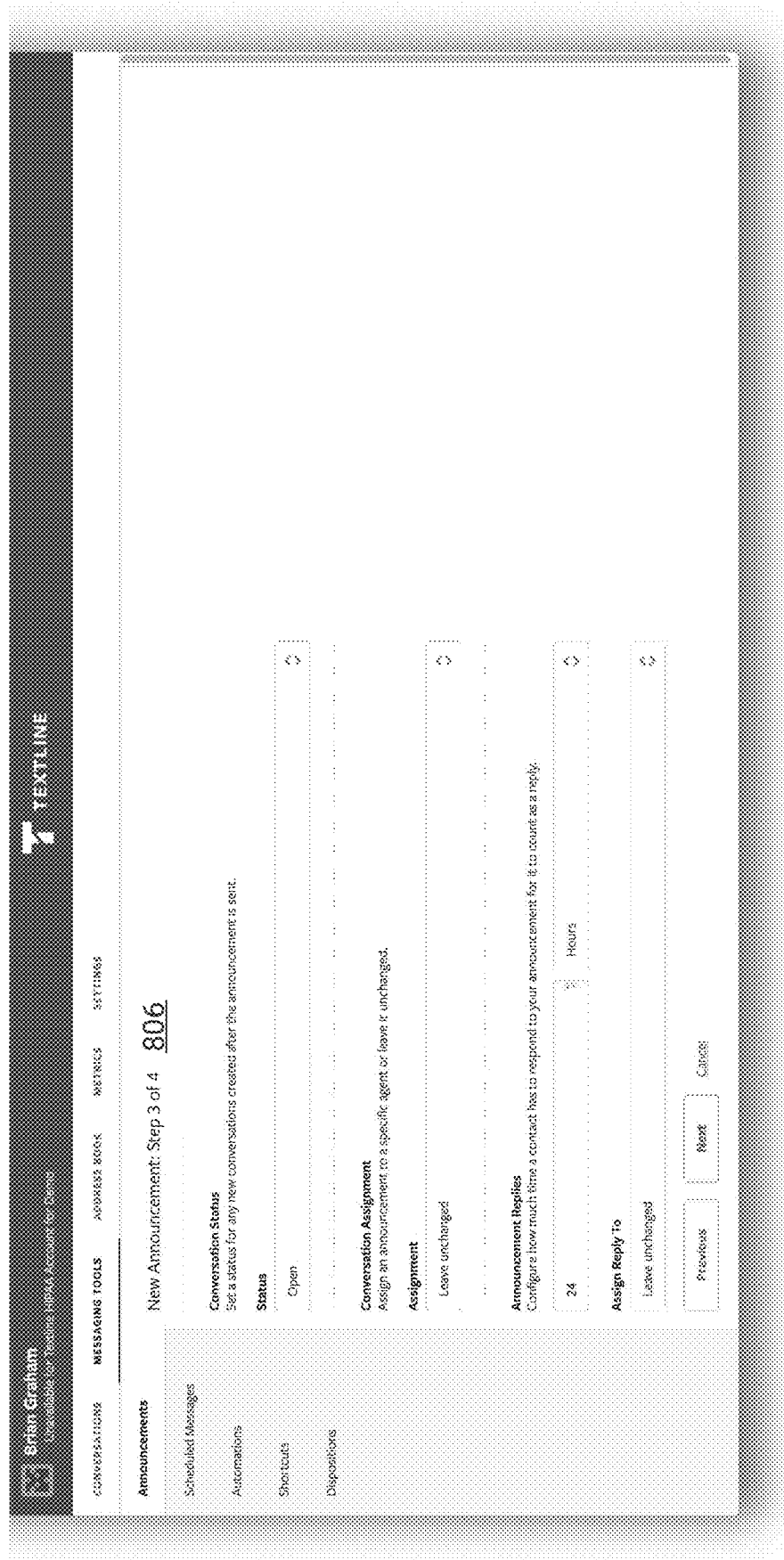
Figure 9A:
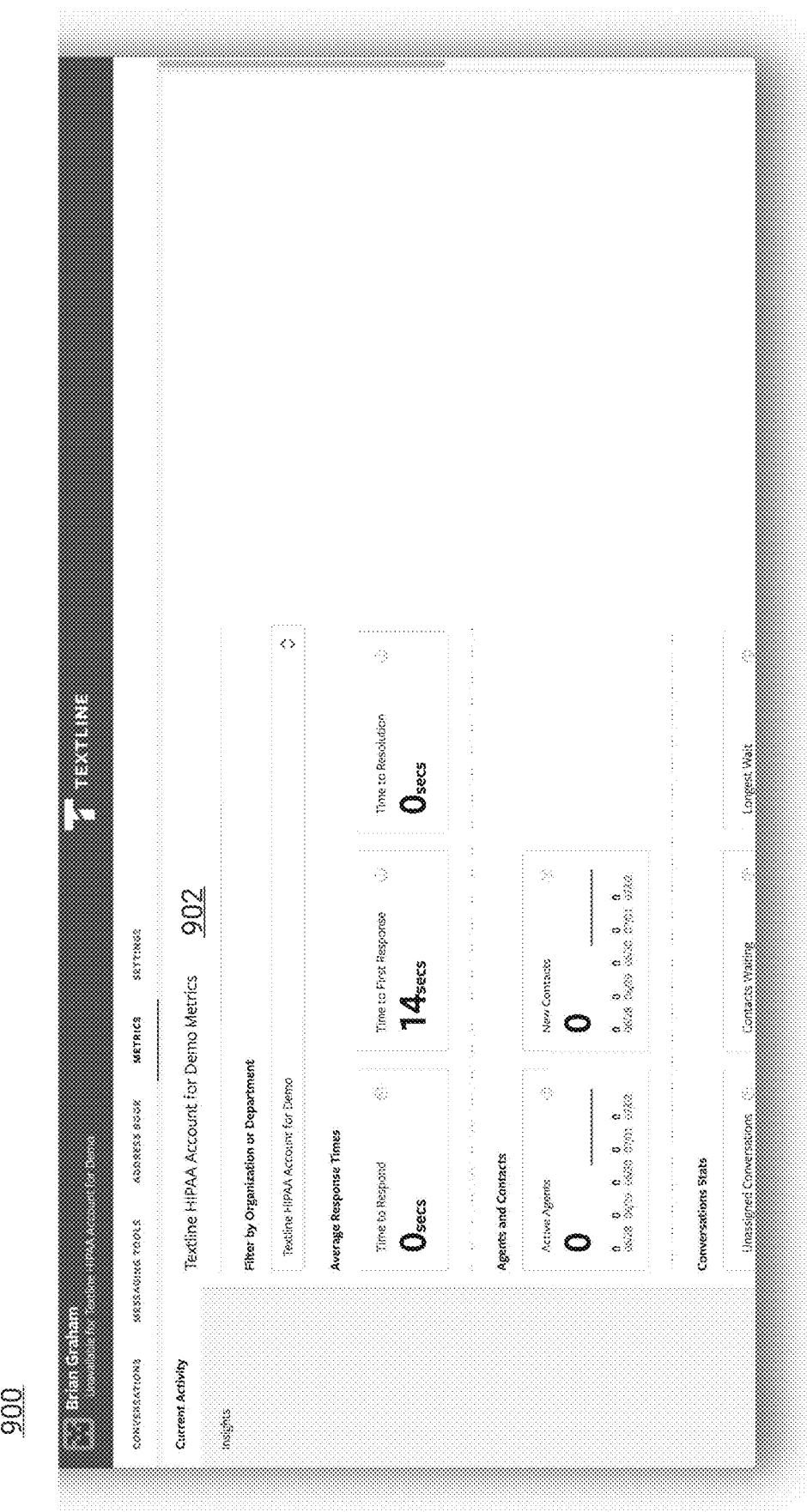
FIGS. 9A-9C are example user interfaces illustrating example metrics associated with messaging.
Figure 9B:
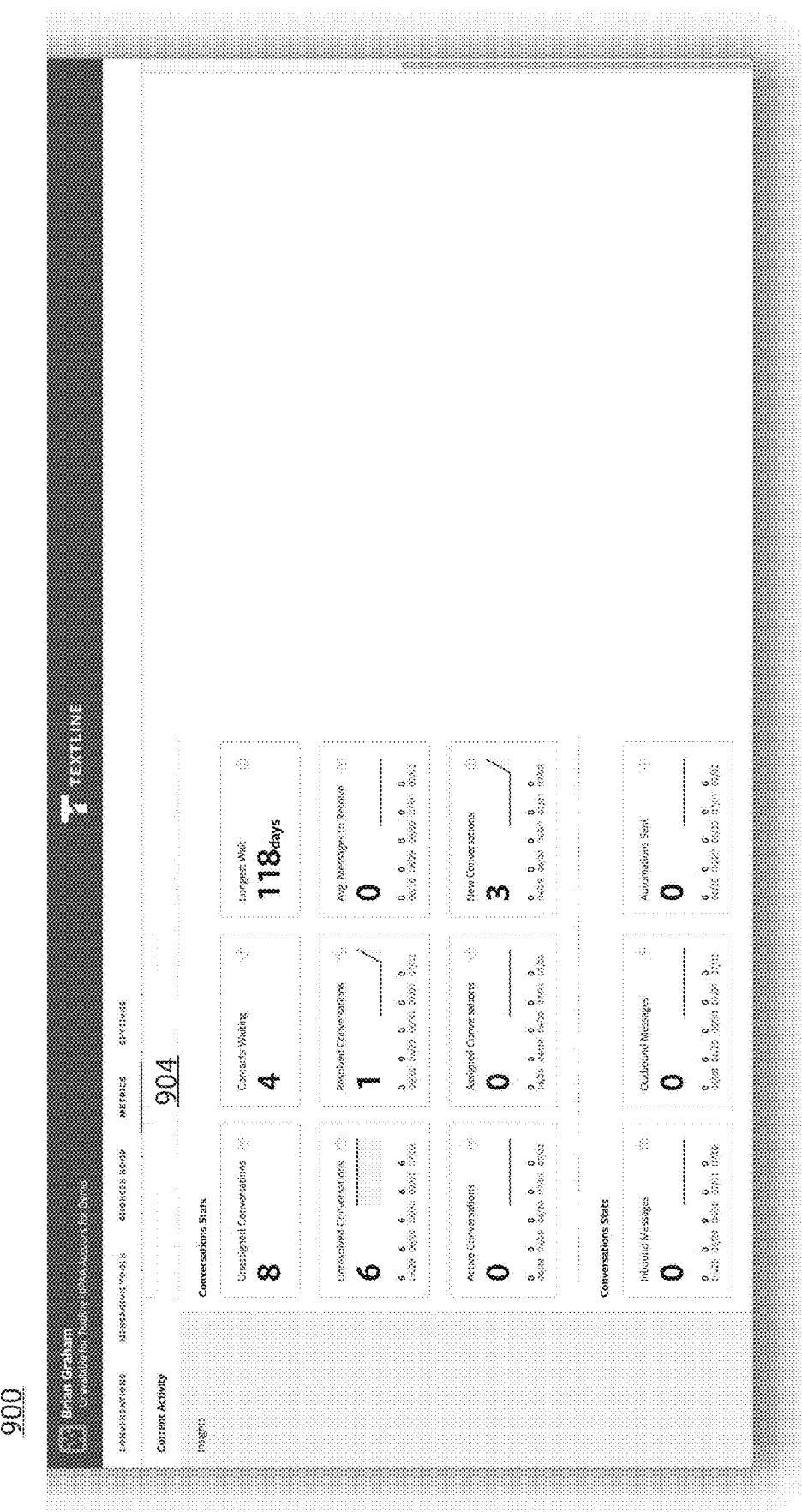
Figure 9C:
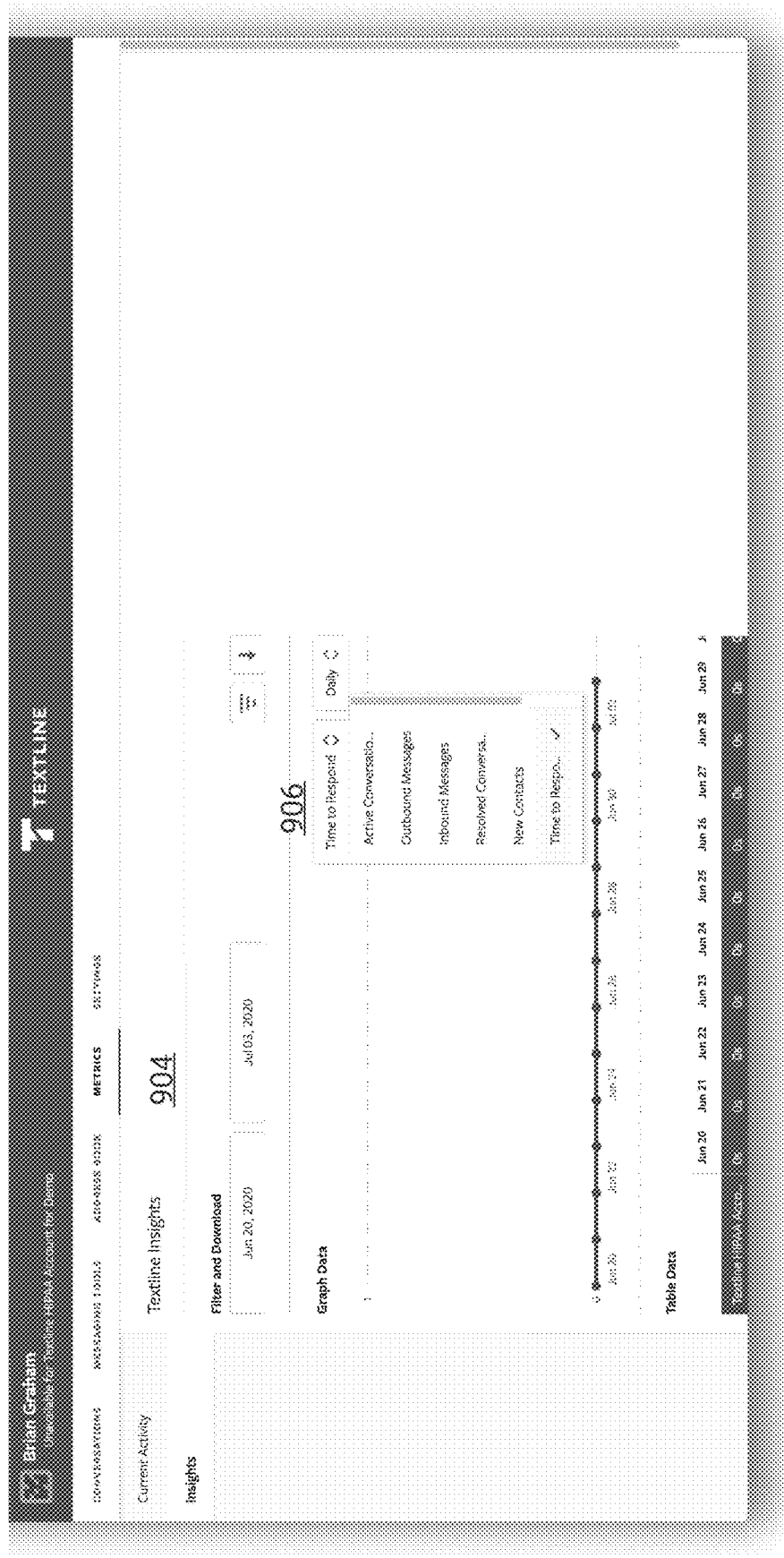

FIG. 8C illustrates the user interface as including a third portion 806. The third portion 806 allows for selection of a conversation status, conversation assignment (e.g., an assignment to a specific customer user), a specification of a specific announcement reply time, and so on. The announcement reply time may indicate an amount of time an end user has to respond to an announcement for the reply to count as a reply. As illustrated in FIGS. 9A-9C, the system 100 may track metrics. An example metric may therefore reflect an extent to which end users respond to particular, or all, announcements.

Figure 8D:
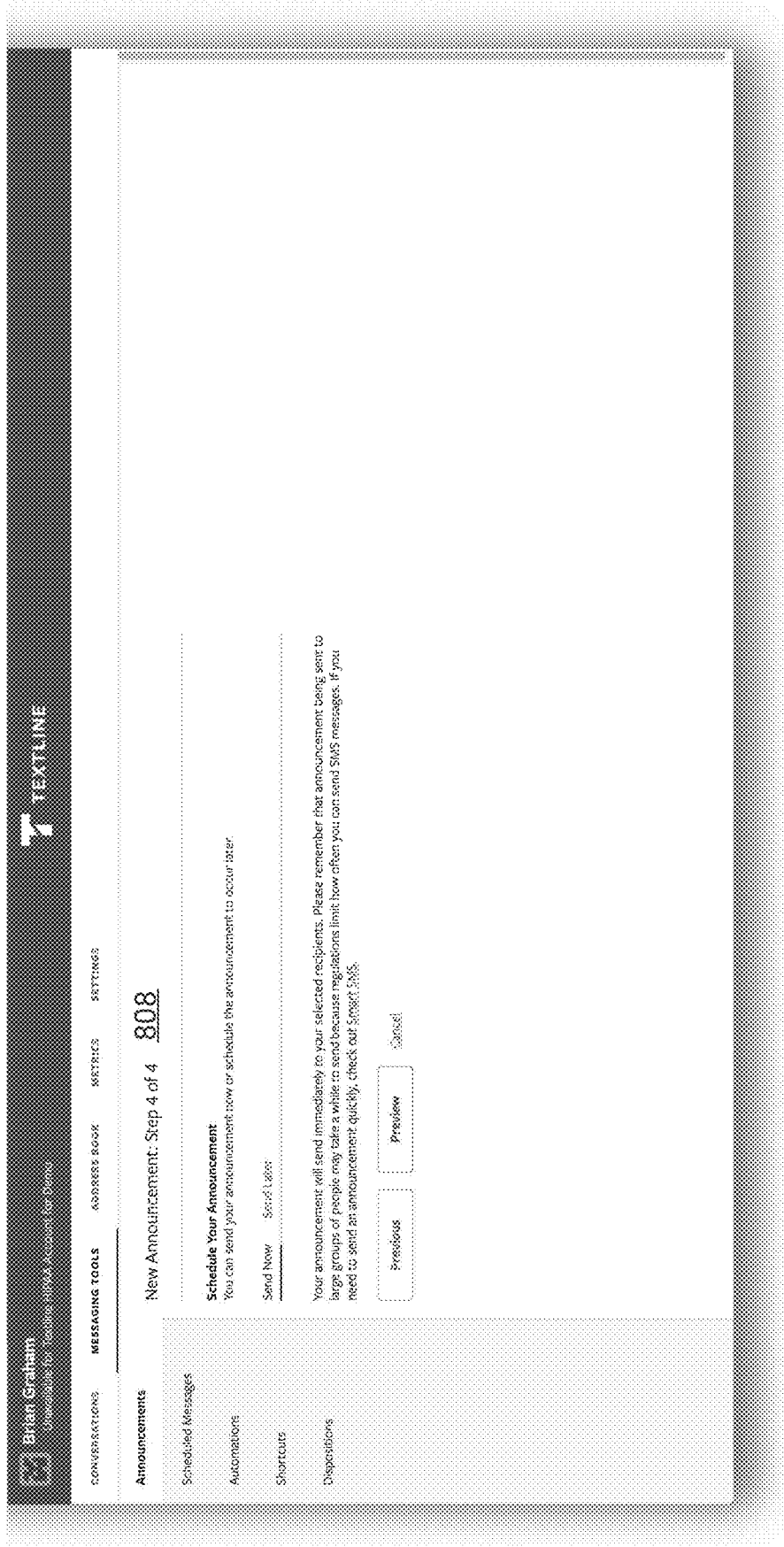

FIG. 8D illustrates the user interface as including a fourth portion 808. The fourth portion 808 allows for the customer user to send the announcement to the end users. The customer user may also schedule a time at which the announcement is to be sent. As described in FIG. 5, in some embodiments the system 100 may validate that each end user selected for the announcement has received affirmative consent.

FIGS. 9A-9C are example user interfaces 900 illustrating example metrics associated with messaging. FIG. 9A illustrates example metrics which are determined by the consent automation system 100. Example metrics may be included in portion 902. The metrics may be filtered according to organization or department associated with an entity. Example metrics may relate to a time to respond, a time to first response, a time to resolution, active agents, and active contacts.

FIG. 9B illustrates additional metrics in portion 904. Example additional metrics may relate to unassigned conversations, contacts waiting, longest wait, unresolved conversations, resolved conversations, average messages to resolve, activate conversations, assigned conversations, new conversations, inbound messages, outbound messages, automations sent (e.g., messages automatically sent as described in FIG. 3C), and so on.

FIG. 9C illustrates detailed graphical representation of specific metrics. For example, a customer user may select amongst options 906 to view a graphical representation of the selected metric. The graphical representation may vary according to time, which the customer user may select (e.g., 'daily', weekly, monthly, and so on).

Manual Override

As described herein, the consent automation system 100 may ensure that end users have affirmatively consented to receiving sensitive information via insecure communication techniques. For example, the system 100 may disallow arbitrary messaging of an end user until the end user has provided an affirmative response to a consent message. In this example, the affirmative response may be provided as a text message to the consent automation system 100 (e.g., a phone number associated with the system 100).

As an example of disallowing arbitrary messaging, a user interface presented to a customer user may constrain actions available to the customer user. For example, the customer user may be unable to provide arbitrary messaging to an end user who has not consented to receiving sensitive information. Instead, and as illustrated in FIG. 7B, the customer user may be limited to interacting with a selectable object which triggers transmission of a consent message. As another example of disallowing arbitrary messaging, a messaging application may be used by a customer user. For this example, the customer user may attempt to message an end user who has not yet provided affirmative consent. The consent automation system 100 may respond to an API request or call from the messaging application, or outside system associated with the messaging application, indicating that the end user has not provided consent. The attempted message may thus be discarded, and a consent message may be provided to the end user. In some embodiments, the consent automation system 100 may be used to route messages to end users and may discard the attempted message.

In the examples described above, the consent automation system 100 may access consent states associated with end users to determine whether affirmative consent has been received. A consent state may, in some embodiments, be set to a default of negative upon any creation, or importation, of an end user into the system 100. Negative may represent a lack of affirmative consent. Upon receipt of affirmative consent for an end user, such as via an affirmative response to a consent message, the system 100 may set a consent state for the end user to positive. Positive may represent receipt of affirmative consent. Thus, customer users may be able to provide arbitrary messages to the end user.

In some embodiments, the consent automation system 100 may allow for manual updating, or adjusting, of a consent state stored by the system 100 (herein referred to as 'manual override'). For example, a customer user may override an end user's consent state to reflect a positive or negative consent state. As will be described, the customer user may use a user interface to override the consent state. With respect to updating the consent state of the end user to be positive, the user interface may initially disallow arbitrary messaging of the end user. Instead, the user interface may limit the customer user to causing transmission of a consent message to the end user. The customer user may interact with a user interface portion to manually update the consent state to be positive. Thus, the customer user may subsequently provide arbitrary messages to the end user.

In this way, the user interface ensures that accidental transmission of sensitive information is avoided. For example, without the user interface limiting the above-described customer user's actions, the customer user could transmit an arbitrary message which includes sensitive information. In this example, and with respect to medical information, the customer user's actions may result in a HIPAA violation.

While the techniques described below relate to manual override of a consent state, in some embodiments an automated updating may be used. As an example, a software agent or application may analyze correspondence or written materials associated with an end user. Example correspondence may include email messages, text messages, application-based messaged (e.g., SLACK), and so on. Example written materials may include a signed contract or agreement. With respect to written materials, the system 100 may obtain scans or images of the materials and may obtain text within the scans or images (e.g., via object character recognition or other techniques).

Within the above-described correspondence or written materials the end user may have provided affirmative consent to receiving sensitive information via insecure communication techniques. For example, correspondence between a customer user (e.g., an employee of a pharmacy) and an end user (e.g., a patient) may have previously occurred which did not use the consent automation system 100. Thus, the system 100 may receive the correspondence (e.g., as an upload) and analyze the correspondence to determine whether affirmative consent has been received. For example, the system 100 may determine whether the end user responded 'YES,' or responded with a different affirmative response, to a consent message as described herein.

In the above-described example, the system 100 may thus automatically set the end user's consent state to be positive from a prior negative consent state. In some embodiments, this automatic setting may occur such that a customer user can arbitrarily message the end user. In some embodiments, the customer user may be initially blocked from arbitrary messaging. For example, a user interface (e.g., the user interface of FIG. 11A) may indicate a lack of affirmative consent and disallow arbitrary messaging. In this example, the user interface may then present information indicating that consent may have been received based on automated analyses of stored information. For example, the user interface may present a portion of correspondence which includes the end user's affirmative consent. In this way, the customer user may validate the correctness of such automated analyses. Upon validation, for example by interacting with a selectable object, the system 100 may update the user interface to allow arbitrary messaging.

The description above, and below, with respect to use of a manual override may, in some embodiments, be understood to include aspects of the remaining disclosure herein. For example, the description of FIGS. 1A-9C may be used to form an understanding of the below. In some embodiments, the manual override option and/or functionality thereof may be used in combination with the description of FIGS. 1A-9C. As an example, the description below focuses on use of a user interface (e.g., of a digital messaging tool). In some embodiments, and as described above, the techniques associated with manual override may be utilized with an intelligent personal assistant. For example, a customer user may provide verbal confirmation that an end user's consent state is to be overridden (e.g., from negative to positive).

Figure 10:
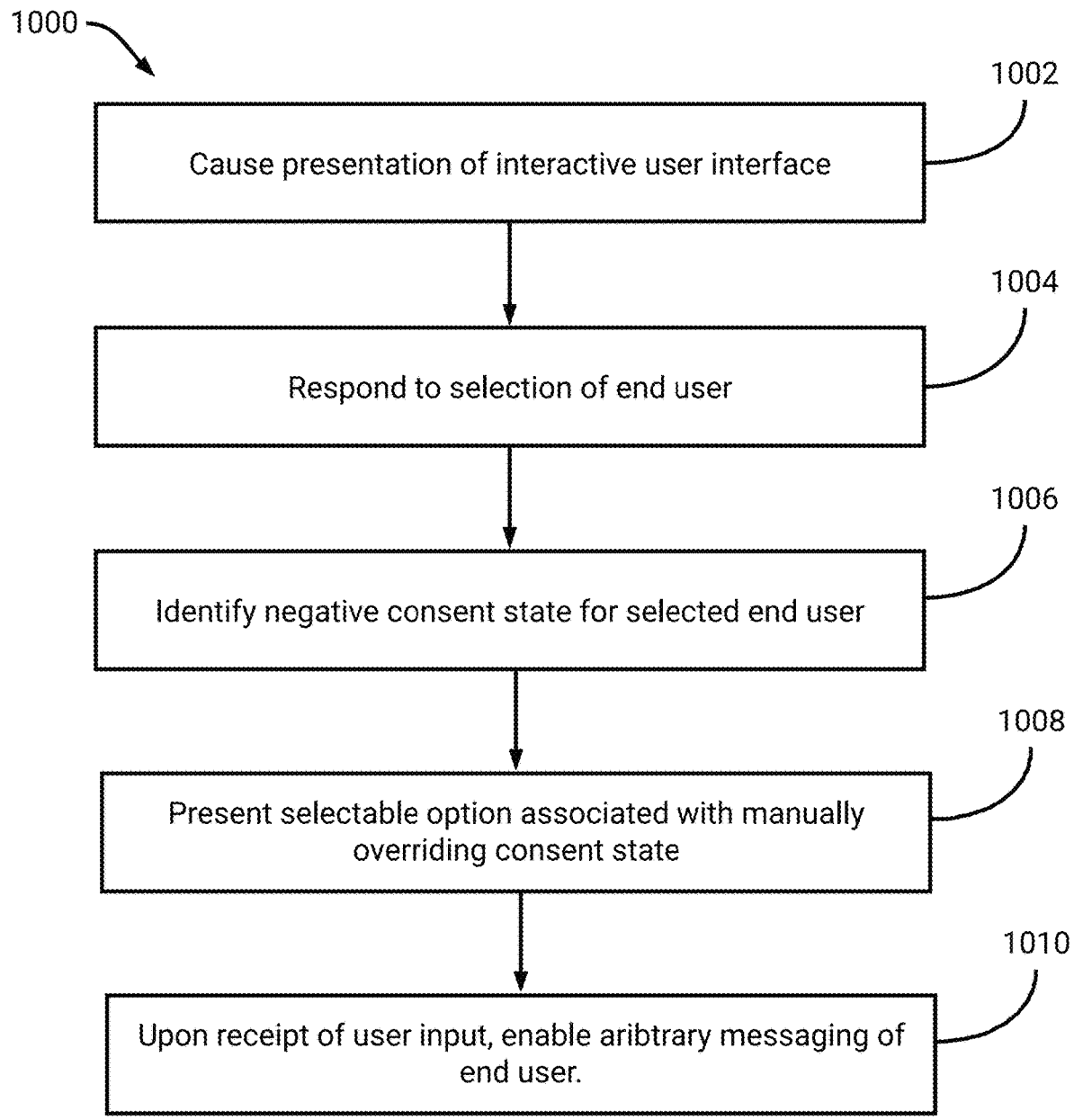
FIG. 10 is a flowchart of an example process for enforcing compliance with manual override.

FIG. 10 is a flowchart of an example process 1000 for enforcing compliance with manual override. For convenience, the process 1000 will be described as being performed by a system of one or more computers (e.g., the consent automation system 100).

At block 1002, the system causes presentation of an interactive user interface. As described with respect to at least FIG. 3A, a customer user associated with an entity may leverage a user interface to provide messages to end users. For example, the user interface may be associated with a digital messaging tool. The user interface may be provided, for example as web information, for rendering on a user device of the customer user. The user interface may also be presented via an application executing the user device and the system may provide information for inclusion in the user interface.

At block 1004, the system responds to selection of an end user. The user interface may be used to select an end user to receive messaging from the customer user. For example, and as described herein with respect to at least FIG. 7A, the customer user may access contact information for the end user.

Optionally, the end user may be newly created within the system. For example, the customer user may provide information associated with the end user. Example information may include a name, phone number or other contact information, and so on. In this example, and as described herein, the system may set a consent state for the end user to be negative.

At block 1006, the system identifies a negative consent state for the end user. As described above, with respect to at least FIG. 3A, the system may determine a consent state for the end user. In the example of FIG. 10, the system identifies the consent state as being negative and thus reflecting a lack of affirmative consent to receiving arbitrary messaging. As described above, the customer user may be constrained to causing transmission of a standardized consent message to the end user (e.g., via a user interface option, such as illustrated in FIG. 7B). In some embodiments, the system may automatically transmit the standardized consent message based on the end user's consent state being negative.

As described herein, the negative consent state may indicate that the end user has not yet responded to a consent message provided to the end user. The negative consent state may also indicate that the end user is newly created and thus has not yet received a consent message. In some embodiments, the negative consent state may indicate that the end user has provided information indicating he/she does not authorize receipt of sensitive information. For example, the end user may have responded negatively to a consent message. As another example, the end user may have revoked previously provided affirmative consent. In some embodiments, the customer user may override the end user's consent state to be positive and thus reflect receipt of affirmative consent (e.g., externally provided affirmative consent).

Figure 11A:
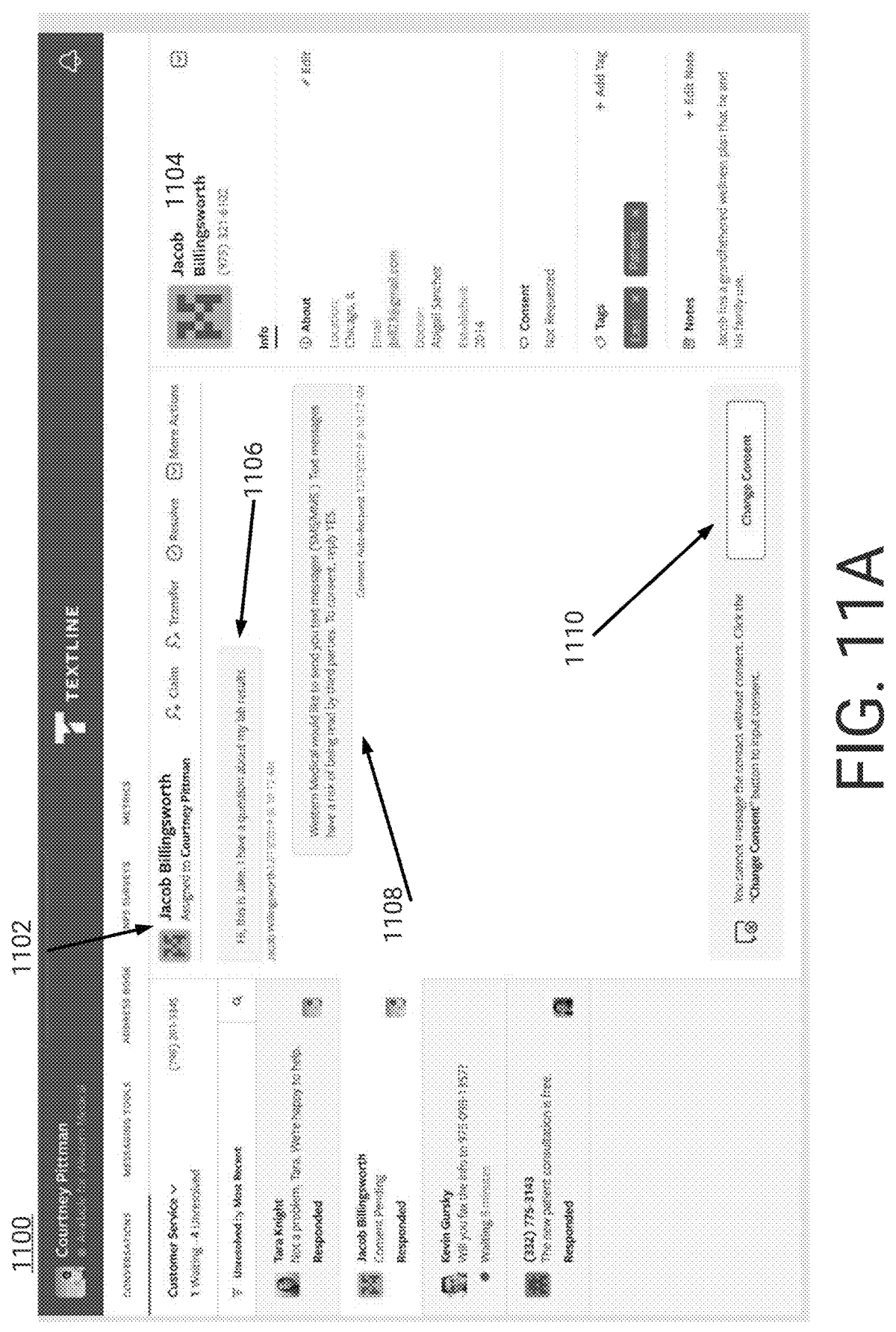
Figure 11B:
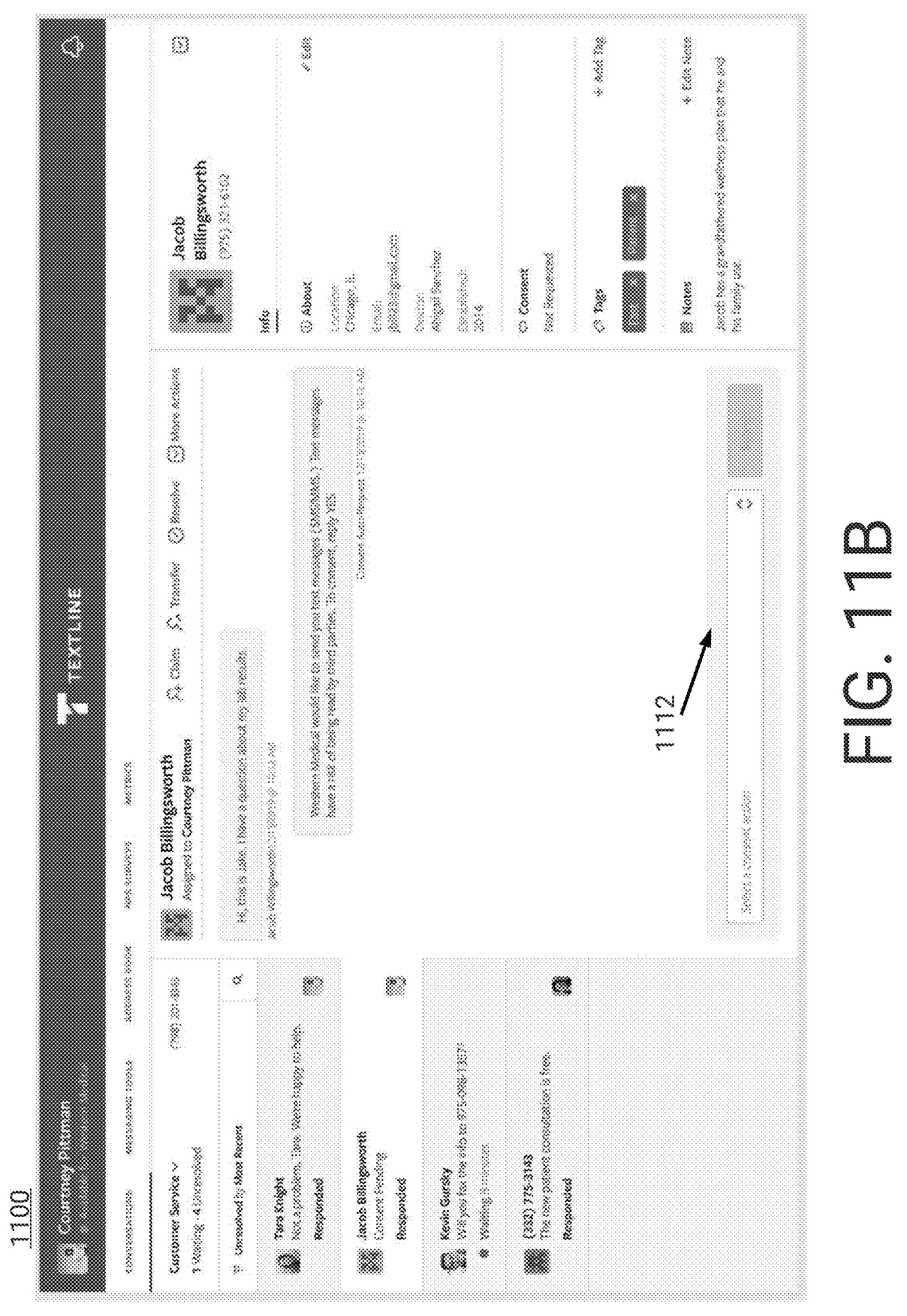
Figure 11C:
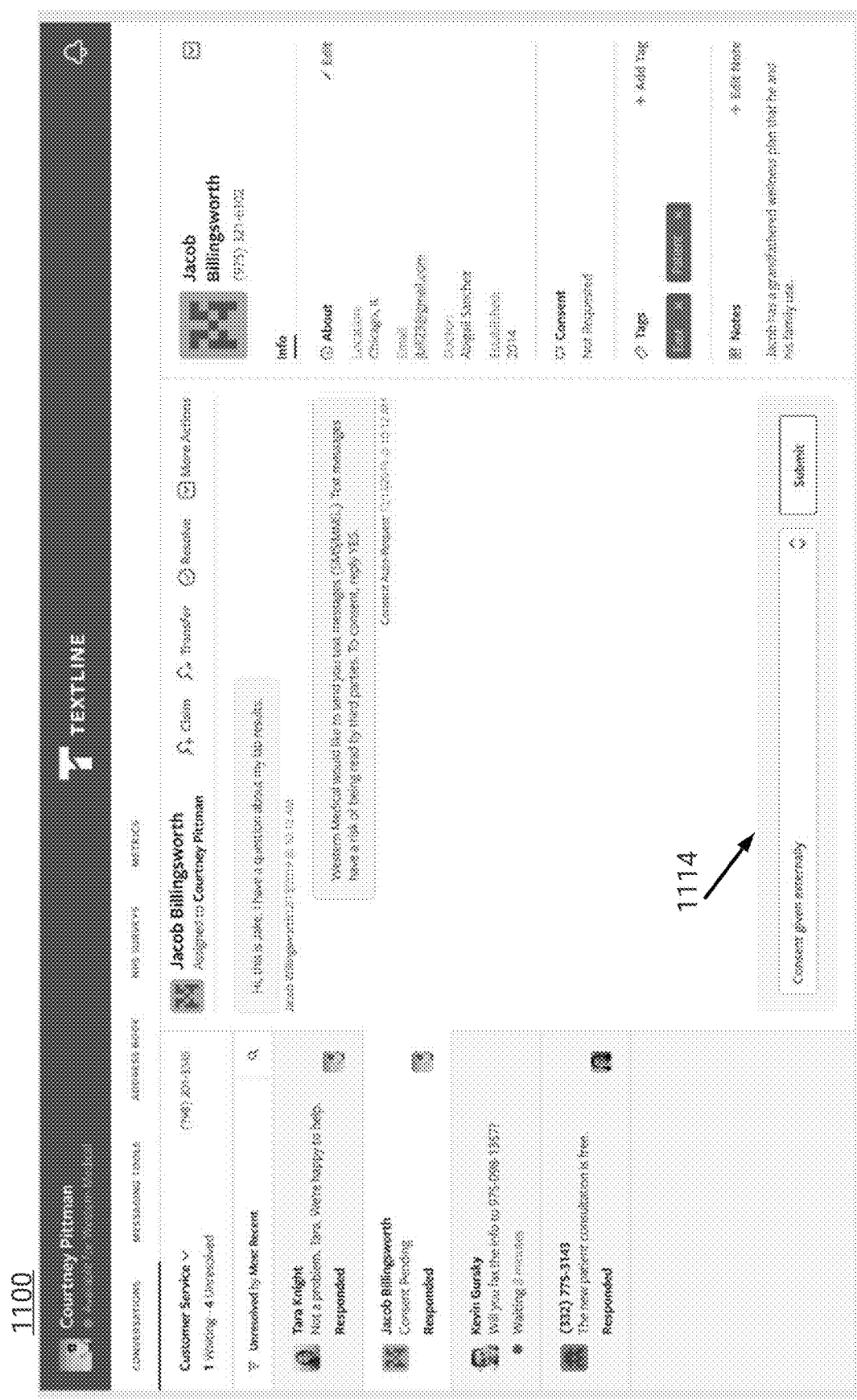

At block 1008, the system presents a selectable, or otherwise interactable, option associated with manually overriding the consent state. The customer user may have access to information indicating that affirmative consent has been received (e.g., affirmative consent was provided externally). For example, the end user may have provided verbal affirmative consent in a phone call with the customer user. As another example, the customer user may have access to written materials (e.g., a contract, agreement) executed by the end user which authorizes receipt of sensitive information via insecure messaging (e.g., texting). An example of the selectable option is illustrated in FIGS. 11B-11C and described below. In some embodiments, the customer user may provide verbal authorization to override the consent state or provide other types of user input as described herein.

In some embodiments, the system may record information indicative of the affirmative consent. For example, and with respect to written materials, the customer user may take an image of the written materials. In this example, the image may be stored by the system as being associated with the end user. As another example, and with respect to a phone call, in some embodiments the phone call may be routed through the system 100 (e.g., via voice over IP). The system may optionally analyze the audio (e.g., using a machine learning model, such as a neural network) to identify a portion of the audio indicative of affirmative consent. The system may also allow the customer user to select a portion of the audio which is indicative of affirmative consent. Thus, the system may optionally store a portion of the phone call which includes the end user providing affirmative consent.

At block 1010, the system receives input to manually override the consent state and enables arbitrary messaging of the end user. The system may receive information indicating selection of the manual override option. For example, the customer user may provide user input to the user interface to identify that affirmative consent has been received. In response, the system may update the consent state for the customer user to reflect a positive consent state. For example, the system may update the consent state as stored in one or more databases (e.g., database 208) to be positive. Based on the positive consent state, the system may cause the user interface to update to allow for arbitrary messaging of the customer user.

While process 1000 focused on use of a user interface, such as the front-end of a digital messaging tool, in some embodiments the process 1000 may be utilized for arbitrary messaging applications. For example, and as described herein, a messaging application may utilize functionality of the system via an application programming interface (API). In this example, the messaging application may provide a request to the system 100 to identify a consent state of the end user. If the consent state is negative, the messaging application or system 100 may disallow arbitrary communications with the end user. As described above, the customer user may thus cause the end user's consent state to be manually updated. For example, the messaging application may provide an API call or request to trigger an update to the end user's consent state. In this example, the messaging application may optionally provide, or optionally be required to provide by the system, a record indicative of affirmative consent (e.g., a portion of audio, an image of an agreement, and so on). For example, the system may cause the messaging application to present a prompt or request for information. In this example, the customer user may respond to the prompt or request with the record. Subsequently, the customer user may be allowed to provide arbitrary messaging to the end user.

FIG. 11A is an example user interface 1100 illustrating identification of an end user who is to be messaged. The user interface 1100, which may be similar to the user interfaces described herein (e.g., user interface 700), is presenting messaging with an end user 1102. Profile information 1104 for the end user is included in the example user interface 1100. In the illustrated example, the end user 1102 has provided an initial message 1106 to a customer user. As described herein, consent states for end users may be defaulted to negative. Thus, since in this example the message 1106 represents an initial interaction with the end user 1102, the end user's consent state is negative. Thus, the user interface 1100 is presenting a standardized consent message 1108 as described herein.

Figure 11D:
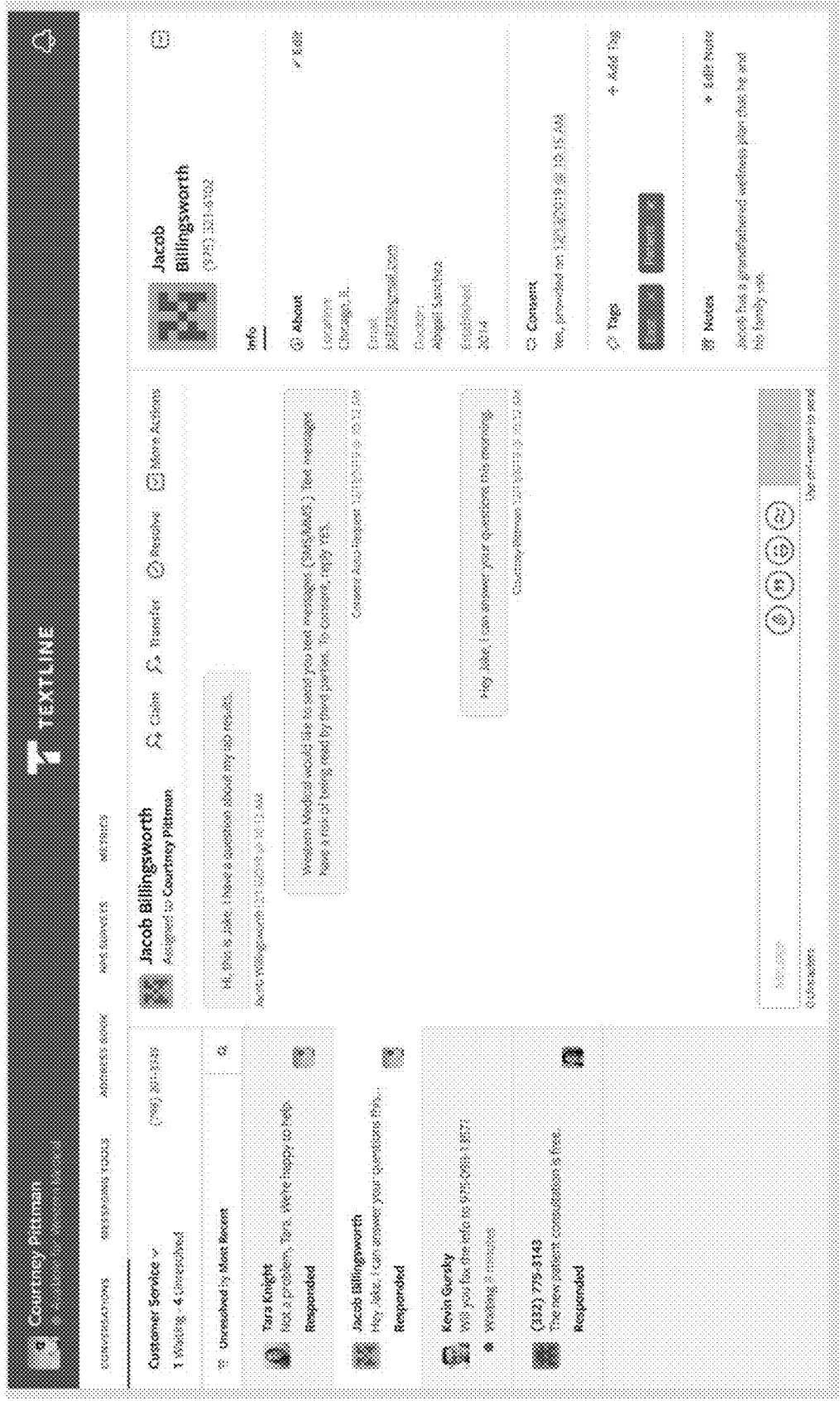
FIG. 11D is an example user interface illustrating arbitrary messaging with the end user.

User interface includes 1100 selectable object 1110 which may be utilized to override the consent state. For example, and as illustrated in FIGS. 11B-11D, the customer user may adjust the end user's 1102 consent state to be positive.

FIGS. 11B-C are example user interfaces 1100 illustrating interaction with a manual override option. In FIG. 11B, the user interface 1100 has been updated to present object 1112. For example, object 1112 may be presented in the user interface 1100 upon interaction with object 1110 in FIG. 11A. In some embodiments, the object 1112 may be presented as a drop-down menu or other user interface portion. With respect to a drop-down menu, FIG. 11C illustrates a customer user as having selected an option 1114 indicative of affirmative consent (e.g., 'consent given externally' option). As described above, this selection may represent the customer user manually overriding the present consent state for the end user. In the illustrated example, the customer user has sent the consent state to be positive. As described herein, the positive consent state may represent that the end user has affirmatively consented to receiving sensitive information, or arbitrary information, via text messaging.

While not illustrated, the customer user can similarly override the consent state for the end user to be negative. For example, the present consent state for the end user may be positive and customer user may have external information indicating that the end user prefers to revoke consent. Thus, the customer user can cause the consent state to be updated (e.g., in database 208) to be negative. As described herein, the user interface 100 may be configured to present a current consent state for the end user such that the customer user may quickly ascertain the consent state.

While not illustrated, in some embodiments the user interface may include a request for information recording the overriding of the end user's consent state (e.g., manual consent by the customer user). As an example, the user interface may include a drag and drop portion on which the customer user may drag a file (e.g., a record) which records, or otherwise indicates, affirmative consent provided by the end user.

FIG. 11D is an example user interface 1100 illustrating arbitrary messaging with the end user. Upon selection that consent was provided externally, for example via object 1114, the system 100 may update (e.g., override) the consent state for the end user. For example, the consent state may be set to positive. Based on the positive consent state, the user interface 1100 may thus update to allow for arbitrary messaging of the end user.

In some embodiments, upon a customer user manually overriding the consent state for the end user, a message may be provided to the end user reflecting that affirmative consent was received. The end user may then respond indicating that affirmative consent should be revoked. For example, the end user may respond using negative language to dispute, or revoke, affirmative consent. The system 100 may then update the end user's consent to be negative, and the customer user may be limited to providing a standardized consent message or may be disallowed from messaging the end user.

Additional Embodiments

All of the processes described herein may be embodied in, and fully automated, via software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence or can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A method implemented by a system of one or more computers, the method comprising:
causing presentation of an interactive user interface to a customer user, the interactive user interface enabling messaging with one or more end users, each end user being associated with a respective phone number;
receiving, via the interactive user interface, selection of a particular end user and updating the interactive user interface to include a selectable option, wherein user input provided to the selectable option triggers transmission of a standardized consent message to a particular phone number associated with the particular end user, the standardized consent message requesting that the particular end user provide affirmative consent to receiving sensitive information;
receiving, via the interactive user interface, user input to indicate receipt of externally provided affirmative consent; and
updating the interactive user interface, wherein the updated interactive user interface includes an input portion configured to receive arbitrary information for transmission to the particular phone number.

2. The method of claim 1, wherein messaging with the one or more end users comprises messaging via SMS or MMS text messages.

3. The method of claim 1, wherein a consent state is maintained for the end user, and wherein receiving user input comprises receiving, via a drop-down menu presented in the interactive user interface, selection of an option to manually override the consent state to reflect affirmative consent.

4. The method of claim 1, further comprising:
maintaining, in one or more databases, respective consent states associated with the end users, each consent state reflecting whether affirmative consent has been received,
wherein actions performable via the interactive user interface are constrained based on the consent state.

5. The method of claim 4, wherein the consent state associated with the particular end user reflects a lack of affirmative consent, and wherein the interactive user interface limits messaging actions to interactions with the selectable option until receipt of the user input.

6. The method of claim 1, further comprising:
obtaining a record reflecting receipt of affirmative consent from the particular end user; and
storing the record as being associated with the particular end user.

7. The method of claim 1, further comprising:
transmitting, to the particular phone number, a confirmation message indicating receipt of affirmative consent.

8. The method of claim 7, further comprising:
receiving, from the particular phone number, a different message indicating revocation or dispute associated with affirmative consent; and
updating a consent state of the particular end user to reflect loss of affirmative consent.

9. A system comprising one or more computer systems and non-transitory computer storage media storing instructions that when executed by the one or more computer systems, cause the one or more computer systems to perform operations comprising:

receiving, from a customer user device via a network, a request to access a digital messaging tool; and
causing rendering, via the customer user device, of an interactive user interface associated with the digital messaging tool, wherein the interactive user interface:
responds to selection of an end user configured to receive text messages, wherein the selection triggers access, by the system, to one or more databases storing a consent state for the end user, the consent state indicating that affirmative consent has not been received from a phone number associated with the end user;
based on the consent state being negative, presents a selectable object to override the consent state, wherein overriding indicates that the end user externally provided affirmative consent, wherein the interactive user interface disallows arbitrary messaging of the end user;
receives user input via the selectable object to override the consent state, wherein the consent state is updated to be positive; and
updates to include an input portion in which arbitrary information may be input, wherein input of arbitrary information is transmitted to the phone number as a text message.

10. The system of claim 9, wherein the interactive user interface:
receives search information usable to identify the end user from a plurality of end users, wherein the system stores identifying information associated with the end users in the one or more databases.

11. The system of claim 9, wherein the digital messaging tool is a web application accessible via the network, and wherein the system stores profile information for a plurality of customer users associated with an entity, wherein the customer users include a customer user associated with the customer user device.

12. The system of claim 9, wherein the interactive user interface:
receives, from the phone number, a different reply message indicating revocation, or dispute, of affirmative consent; and
updates to remove the input portion.

13. The system of claim 9, wherein the selectable object is a drop-down menu.

14. The system of claim 9, wherein the interactive user interface:
updates to include a portion on which a record of the externally received affirmative consent is configured to be provided.

15. A system comprising one or more computer systems and non-transitory computer storage media storing instructions that when executed by the one or more computer systems, cause the one or more computer systems to perform operations comprising:
causing presentation of an interactive user interface to a customer user, the interactive user interface enabling messaging with one or more end users, each end user being associated with a respective phone number;
receiving, via the interactive user interface, selection of a particular end user and updating the interactive user interface to include a selectable option, wherein user input provided to the selectable option triggers transmission of a standardized consent message to a particular phone number associated with the particular end user, the standardized consent message requesting that the particular end user provide affirmative consent to receiving sensitive information;

receiving, via the interactive user interface, user input to indicate receipt of externally provided affirmative consent; and updating the interactive user interface, wherein the updated interactive user interface includes an input portion configured to receive arbitrary information for transmission to the particular phone number.

16. The system of claim 15, wherein messaging with the one or more end users comprises messaging via SMS or MMS text messages.

17. The system of claim 15, wherein a consent state is maintained for the end user, and wherein receiving user input comprises receiving, via a drop-down menu presented in the interactive user interface, selection of an option to manually override the consent state to reflect affirmative consent.

18. The system of claim 15, wherein the operations further comprise:

obtaining a record reflecting receipt of affirmative consent from the particular end user; and storing the record as being associated with the particular end user.

19. The system of claim 15, wherein the operations further comprise:

transmitting, to the particular phone number, a confirmation message indicating receipt of affirmative consent.

20. The system of claim 19, wherein the operations further comprise:

receiving, from the particular phone number, a different message indicating revocation, or dispute, of affirmative consent; and updating a consent state of the particular end user to reflect loss of affirmative consent.

* * * * *